(12) United States Patent
Morris et al.

(10) Patent No.: US 10,765,331 B2
(45) Date of Patent: Sep. 8, 2020

(54) WEARABLE PULSE SENSING DEVICE SIGNAL QUALITY ESTIMATION

(71) Applicant: Microsoft Technology Licensing, LLC, Redmond, WA (US)

(72) Inventors: Daniel Morris, Bellevue, WA (US); Sumit Basu, Seattle, WA (US); Jeremiah Wander, Seattle, WA (US); Gregory R. Smith, Bellevue, WA (US); T. Scott Saponas, Woodinville, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1206 days.

(21) Appl. No.: 14/750,037

(22) Filed: Jun. 25, 2015

(65) Prior Publication Data
US 2016/0287110 A1 Oct. 6, 2016

Related U.S. Application Data

(60) Provisional application No. 62/142,463, filed on Apr. 2, 2015.

(51) Int. Cl.
*A61B 5/024* (2006.01)
*A61B 5/00* (2006.01)
*A61B 5/021* (2006.01)

(52) U.S. Cl.
CPC .......... *A61B 5/02438* (2013.01); *A61B 5/024* (2013.01); *A61B 5/02416* (2013.01);
(Continued)

(58) Field of Classification Search
CPC .......................... A61B 5/02416; A61B 5/0261
See application file for complete search history.

(56) References Cited

U.S. PATENT DOCUMENTS

| 4,830,017 A | 5/1989 | Perry et al. |
| 8,768,440 B1 | 7/2014 | Brodnick et al. |

(Continued)

FOREIGN PATENT DOCUMENTS

| CN | 102270264 A | 12/2011 |
| CN | 103020472 A | 4/2013 |

(Continued)

OTHER PUBLICATIONS

"H2: The First Wearable Blood Pressure Monitor", Indiegogo Website, Available Online at https://www.indiegogo.com/projects/h2-the-first-wearable-blood-pressure-monitor#/, Available as Early as Oct. 31, 2014, 32 pages.

(Continued)

*Primary Examiner* — Hien N Nguyen
(74) *Attorney, Agent, or Firm* — Alleman Hall Creasman & Tuttle LLP

(57) ABSTRACT

A first data window of a pulse waveform signal comprising a first number of samples is analyzed to determine a level of confidence that a pulse sensing device is placed correctly. If an initial level of confidence is met, the user is given positive feedback, and a second data window of a pulse waveform signal comprising a second, larger number of samples is analyzed. If an increased level of confidence is met, the user is given increased positive feedback. If a level of confidence is not met, the user is given negative feedback. If a final level of confidence is met, the user is given feedback that the pulse sensing device is placed correctly.

20 Claims, 9 Drawing Sheets

(52) U.S. Cl.
CPC .......... *A61B 5/489* (2013.01); *A61B 5/7207* (2013.01); *A61B 5/7221* (2013.01); *A61B 5/7264* (2013.01); *A61B 5/02108* (2013.01); *A61B 5/681* (2013.01)

(56) References Cited

U.S. PATENT DOCUMENTS

| | | |
|---|---|---|
| 2004/0138540 A1 | 7/2004 | Baker et al. |
| 2005/0234286 A1 | 10/2005 | Riehl et al. |
| 2010/0130873 A1 | 5/2010 | Yuen et al. |
| 2010/0298728 A1 | 11/2010 | Addison et al. |
| 2011/0077484 A1 | 3/2011 | Van Slyke et al. |
| 2011/0184297 A1 | 7/2011 | Vitali et al. |
| 2013/0267796 A1 | 10/2013 | Enric Monte Moreno |

FOREIGN PATENT DOCUMENTS

| | | |
|---|---|---|
| CN | 103300852 A | 9/2013 |
| CN | 103845038 A | 6/2014 |
| CN | 104042208 A | 9/2014 |
| CN | 104274191 A | 1/2015 |
| CN | 104462744 A | 3/2015 |
| JP | H1170089 A | 3/1999 |
| KR | 101349767 B1 | 1/2014 |
| KR | 101485700 B1 | 1/2015 |
| KR | 1020150092465 A | 8/2015 |
| KR | 1020160092250 A | 8/2016 |
| KR | 101667412 B1 | 10/2016 |
| WO | 2005015814 A1 | 2/2005 |
| WO | 2006094107 A1 | 9/2006 |
| WO | 2013036718 A1 | 3/2013 |
| WO | 2014107795 A1 | 7/2014 |
| WO | 2015033327 A1 | 3/2015 |

OTHER PUBLICATIONS

IPEA European Patent Office, International Preliminary Report on Patentability Issued in PCT Application No. PCT/US2016/025458, dated Jan. 16, 2017, WIPO, 7 Pages.

Viola, P. et al., "Rapid Object Detection using a Boosted Cascade of Simple Features", 2001 IEEE Computer Society Conference on Computer Vision and Pattern Recognition, vol. 1, Jan. 1, 2001, 16 pages.

ISA European Patent Office, International Search Report and Written Opinion Issued in PCT Application No. PCT/US2016/025458, dated Oct. 18, 2016, WIPO, 19 pages.

Morris, Dan et al., "Video-Based Pulse Measurement," U.S. Appl. No. 14/257,671, filed Apr. 21, 2014, 54 pages.

Rio, et al., "Assessment of Different Methods to Estimate Electrocardiogram Signal Quality", In Proceedings of Computing in Cardiology, Sep. 8, 2011, pp. 609-612.

Foo, et al., "Adaptive Algorithms to Optimise Photoplethysmographic Signals in Heart Rate Estimation", In Biomedical Engineering, vol. 3, Mar. 25, 2015, 2 pages.

Foo, et al., "Variability in Heart Rate Estimates from Different Pulse Oximeters", In Biomedical Engineering, vol. 3, Mar. 25, 2015, 2 pages.

Bansal, et al., "Algorithm for Online Detection of HRV From Coherent ECG and Carotid Pulse Wave", In International Journal of Biomedical Engineering and Technology, vol. 14, No. 4, Apr. 21, 2014, 2 pages.

Springer, et al., "Robust Heart Rate Estimation From Noisy Phonocardiograms", In Proceedings of Computing in Cardiology Conference, Sep. 7, 2014, pp. 613-616.

Nidhal, et al., "Computerized Algorithm for Fetal Heart Rate Baseline and Baseline Variability Estimation based on Distance Between Signal Average and a Value", In International Journal Pharmacol, Mar. 16, 2011, 11 pages.

Asada, et al., "Mobile Monitoring with Wearable Photoplethysmographic Biosensors", In Proceedings of IEEE Engineering in Medicine and Biology Magazine, vol. 22, Issue 3, May 2003, pp. 28-40.

Asada, et al., "Active Noise Cancellation using MEMS Accelerometers for Motion-Tolerant Wearable Bio-Sensors", In Proceedings of 26th Annual International Conference of the IEEE Engineering in Medicine and Biology Society, vol. 1, Sep. 1, 2004, pp. 2157-2160.

Breiman, et al., "Classification and Regression Trees", In Proceedings of Chapman and Hall/CRC, Jan. 1, 1984, 5 pages.

"Heart Disease and Stroke Prevention", Retrieved on: Apr. 1, 2015 Available at: http://www.cdc.gov/chronicdisease/resources/publications/AAG/dhdsp.htm.

"How much physical activity do adults need?", Retrieved on: Apr. 1, 2015 Available at: http://www.cdc.gov/physicalactivity/everyone/guidelines/adults.hmtl.

Ceesay, et al., "The Use of Heart Rate Monitoring in the Estimation of Energy Expenditure: A Validation Study Using Indirect Whole-Body Calorimetry", In British Journal of Nutrition, vol. 61, Issue 02, Mar. 1989, pp. 175-186.

Cliord, et al., "Signal Quality Indices and Data Fusion for Determining Clinical Acceptability of Electrocardiograms", In Physiological measurement, Sep. 2012, 19 pages.

Cole, et al., "Heart-Rate Recovery Immediately after Exercise as a Predictor of Mortality", In the New England Journal of Medicine, vol. 341, No. 18, Oct. 28, 1999, pp. 1351-1357.

"Health Statistics—Atlas on Mortality in the European Union 2009", In Proceedings of European Communities, Aug. 30, 2009, 2 pages.

Farooq, et al., "PPG Delineator for Real-Time Ubiquitous Applications", In Proceedings of IEEE Annual International Conference of the Engineering in Medicine and Biology Society, Aug. 31, 2010, pp. 4582-4585.

Fox, et al., "Tracking for Health", In Pew Research Center, Jan. 28, 2013, 40 pages.

Gibbs, et al., "Active Motion Artifact Cancellation for Wearable Health Monitoring Sensors Using Collocated Mems Accelerometers", In Proceedings of SPIE 5765, Smart Structures and Materials: Sensors and Smart Structures Technologies for Civil, Mechanical, and Aerospace Systems, Jun. 3, 2005, 2 pages.

Hoyert, et al., "Deaths: Preliminary Data for 2011", In National Vital Statistics Reports, vol. 61, No. 6, Oct. 10, 2012, pp. 1-52.

Karlen, et al., "Photoplethysmogram Signal Quality Estimation using Repeated Gaussian Filters and Cross-Correlation", In Physiological Measurement, vol. 33, Issue 10, Sep. 18, 2012, pp. 1617-1629.

Karlen, et al., "Adaptive Pulse Segmentation and Artifact Detection in Photoplethysmography for Mobile Applications", In Proceedings of Annual International Conference of the IEEE Engineering in Medicine and Biology Society, Aug. 28, 2012, pp. 3131-3134.

Karlen, et al., "Photoplethysmogram Processing Using an Adaptive Single Frequency Phase Vocoder Algorithm", In Proceedings of 4th International Joint Conference on Biomedical Engineering Systems and Technologies, Jan. 26, 2011, 6 pages.

Krishnan, et al., "Two-Stage Approach for Detection and Reduction of Motion Artifacts in Photoplethysmographic Data", In Proceedings of IEEE Transactions on Biomedical Engineering, vol. 57, No. 8, Feb. 17, 2010, pp. 1867-1876.

Leon, et al., "Cardiac Rehabilitation and Secondary Prevention of Coronary Heart Disease", In Circulation, vol. 111, Issue 13, Jan. 25, 2005, pp. 369-376.

Li, et al., "Dynamic Time Warping and Machine Learning for Signal Quality Assessment of Pulsatile Signals", In Physiological Measurement, vol. 33, No. 9, Aug. 17, 2012, 2 pages.

Li, et al., "Robust Heart Rate Estimation from Multiple Asynchronous Noisy Sources using Signal Quality Indices and a Kalman Filter", In Physiological Measurement, vol. 29, No. 1, Feb. 29, 2008, pp. 1-22.

Mancia, et al., "2013 ESH/ESC Guidelines for the Management of Arterial Hypertension", In European Heart Journal, vol. 34, Issue 28, Jun. 14, 2013, pp. 1-72.

Mannheimer, "The Light-Tissue Interaction of Pulse Oximetry", In Official Journal of International Anesthesia Research Society, Anesthesia and Analgesia, vol. 105, Issue 6, Dec. 2007, 7 pages.

(56) References Cited

OTHER PUBLICATIONS

Nelson, et al., "Noninvasive Measurement of Central Vascular Pressures with Arterial Tonometry: Clinical Revival of the Pulse Pressure Waveform?", In Journal of Mayo Clinic, vol. 85, Issue 5, May 2010, pp. 460-472.

Nilsson, et al., "Monitoring of Respiratory Rate in Postoperative Care using a New Photoplethysmographic Technique", In Journal of Clinical Monitoring and Computing, vol. 16, Issue 4, May 2000, 6 pages.

Patterson, et al., "Ratiometric Artifact Reduction in Low Power Reflective Photoplethysmography", In Proceedings of IEEE Transactions on Biomedical Circuits and Systems, vol. 5, No. 4, Jul. 14, 2011, pp. 330-338.

Rhee, et al., "Artifact-Resistant Power-Efficient Design of Finger-Ring Plethysmographic Sensors", In IEEE Transactions on Biomedical Engineering, vol. 48, Issue 7, Jul. 2011, 11 Pages.

Schafer, et al., "How Accurate is Pulse Rate Variability as an Estimate of Heart Rate Variability? A Review on Studies Comparing Photoplethysmographic Technology with an Electrocardiogram", In International Journal of Cardiology, Jun. 5, 2013, 2 pages.

Silva, et al., "Signal Quality Estimation With Multichannel Adaptive Filtering in Intensive Care Settings", In IEEE Transactions on Biomedical Engineering, vol. 59, Issue 9, Sep. 2012, 10 pages.

Smith, et al., "Pulse Transit Time: An Appraisal of Potential Clinical Applications", In Thorax vol. 54, Issue 5, May 1999, 6 pages.

Sukor, et al., "Signal Quality Measures for Pulse Oximetry through Waveform Morphology Analysis", In Proceedings of Physiological Measurement, vol. 32, Issue 3, Mar. 2011, 2 pages.

Brown, et al., "Exercise-Based Rehabilitation for Patients with Coronary Heart Disease: Systematic Review and Meta-Analysis of Randomized Controlled Trials", In the American journal of Medicine, vol. 116, Issue10, May 2015, 2 pages.

Weng, et al., "An Improved Pre-processing Approach for Photoplethysmographic Signal", In Proceedings of 27th Annual Conference Engineering in Medicine and Biology, Sep. 1, 2005, 2 pages.

Wood, et al., "Noise Cancellation Model Validation for Reduced Motion Artifact Wearable PPG Sensors using Mems Accelerometers", In IEEE Journal of Biomedical and Health Informatics, vol. 18 Issue 2, Mar. 2014, 12 pages.

Wood, et al., "A Motion-Tolerant Adaptive Algorithm for Wearable Photoplethysmographic Biosensors", : In IEEE Journal of Biomedical and Health Informatics, vol. 18 Issue 2, Mar. 2014, 12 pages.

Wander, et al., "A Combined Segmenting and Non-Segmenting Approach to Signal Quality Estimation for Ambulatory Photoplethysmography", In Physiological Measurement, vol. 35, Issue 12, Dec. 2014, 2 pages.

U.S. Appl. No. 14/500,459, Saponas, et al., "Wearable Pulse Pressure Wave Sensing Device", filed Sep. 29, 2014.

Wander, et al., "A Combined Segmenting and Non-Segmenting Approach to Signal Quality Estimation for Ambulatory Photoplethysmography", In Journal of Physiological Measurement, vol. 35, No. 12, Nov. 19, 2014, pp. 2543-2561.

"Office Action and Search Report Issued in Chinese Patent Application No. 201680024469.6", dated Dec. 3, 2019, 17 Pages.

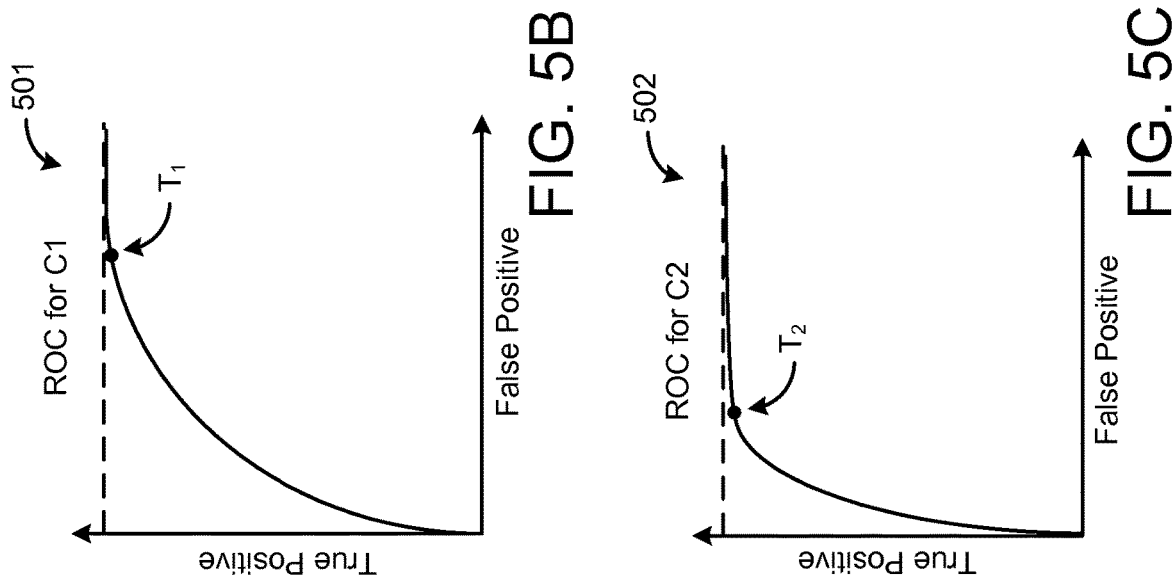
FIG. 5B
FIG. 5C
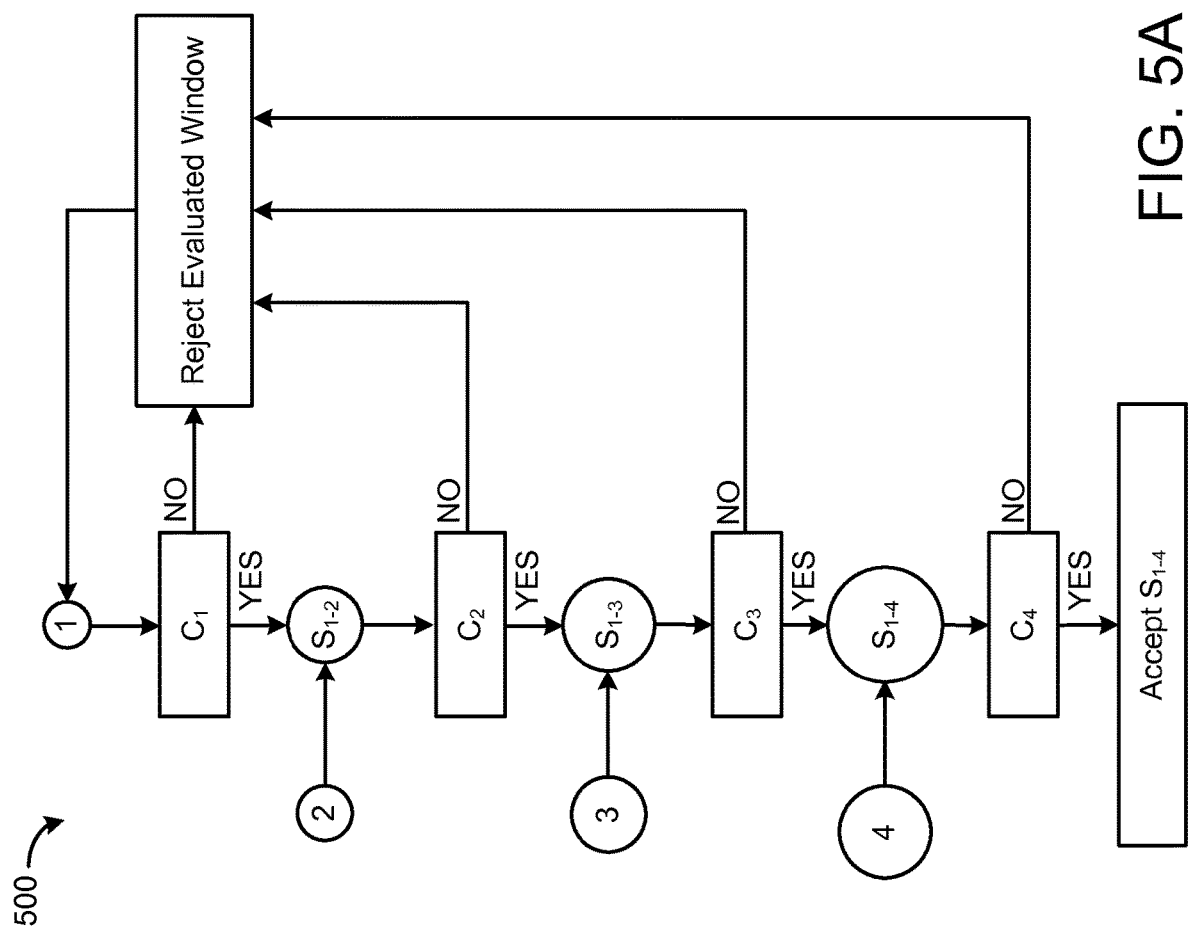
FIG. 5A

WEARABLE PULSE SENSING DEVICE SIGNAL QUALITY ESTIMATION

CROSS REFERENCE TO RELATED APPLICATIONS

This application claims priority to U.S. Provisional Patent Application No. 62/142,463, filed Apr. 2, 2015, the entirety of which is hereby incorporated herein by reference.

BACKGROUND

Monitoring heart rate levels provides useful health information. A pulse pressure wave sensor provides a non-invasive mechanism for capturing the morphology of the pulse pressure wave which can be used in measuring heart rate, heart rate variability, arterial pressure, pulse wave velocity, and augmentation index. A pulse pressure wave sensor may be incorporated into a wearable device.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A first data window of a pulse waveform signal comprising a first number of samples is analyzed to determine a level of confidence that a pulse sensing device is placed correctly. If an initial level of confidence is met, the user is given positive feedback, and a second data window of a pulse waveform signal comprising a second, larger number of samples is analyzed. If an increased level of confidence is met, the user is given increased positive feedback. If a level of confidence is not met, the user is given negative feedback. If a final level of confidence is met, the user is given feedback that the pulse sensing device is placed correctly.

BRIEF DESCRIPTION OF THE DRAWINGS

FIG. 5A shows a flow chart for an example cascading classifier.

FIGS. 5B and 5C show example receiver operating characteristic curves and threshold selections for a cascading classifier.

DETAILED DESCRIPTION

Figure 1:
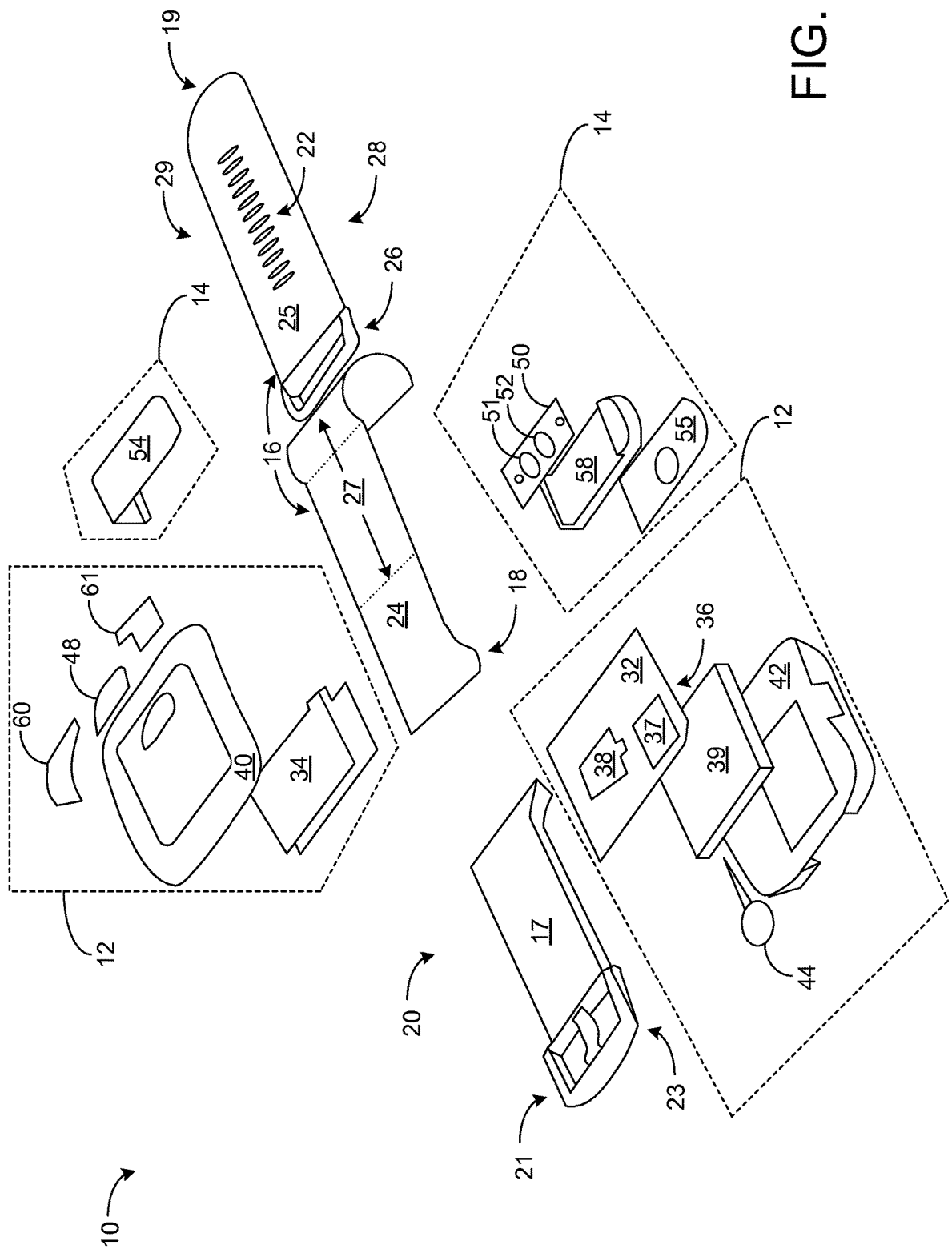
FIG. 1 shows an exploded view of an example wearable electronic device.

Continuous cardiac monitoring of healthy and unhealthy patients can help understand the progression of heart disease and enable early treatment. Wearable cardiovascular monitors, such as wrist-worn cardiovascular monitoring devices, can provide continuous monitoring outside of a clinical setting. Both optical and pressure-based sensing of the pulse pressure wave offer non-invasive approaches to extracting important cardiovascular parameters, such as heart rate, augmentation index, and pulse wave velocity.

The accuracy and quantity of parameters that can be extracted is dependent on the resolution of the pulse waveform signal. However, both optical and pressure-based sensing devices are susceptible to corruption from a number of noise sources including motion artifacts, and both are sensitive to sensor placement and contact quality. Optical sensors are susceptible to contamination from multiple sources. If the device is not being worn correctly, or there is poor physical contact between the photosensor and the wearer's tissue, ambient light will contaminate, or possibly saturate the photosensor. Further, even if the interface between the photosensor and tissue is good, fluid flow in the tissue associated with movement or pressure changes (i.e., not associated with the heart's pumping of blood) will also appear in the measured pulse waveform signal. For pressure-based sensors, movement and muscle contraction also affect the pressure observed at the sensor.

A number of approaches have been developed to mitigate or remove motion artifacts from measured pulse waves. For example, a motion signal may be acquired concurrently with the pulse waveform signal using one or more motion sensors. The motion signal may then be filtered from the pulse waveform signal. However, this is an especially difficult task in the presence of artifact caused by ambulation (e.g., walking or jogging), which shares significant spectral energy with the true pulse waveform signal. Filtering the motion signal from the pulse waveform signal may thus result in the filtering of the actual pulse waveform signal, leaving only artifact.

Therefore, when such sensors are applied—particularly in the context of non-expert users applying wearable devices—some amount of automatic signal quality estimation can be used to confirm that the user has correctly placed the sensor. Furthermore, even when the sensor is placed correctly, automatic signal quality estimation can be used to separate corrupted data from valid data, prior to any analysis of the raw signal.

According to the present disclosure, a wearable cardiovascular monitoring device is configured to automatically determine the signal quality of a pulse waveform signal. In one example, a classifier cascade is utilized to analyze data windows of progressively increasing size with progressively increasing scrutiny. User feedback is provided at each stage to indicate a confidence level that the current sensor placement is the correct sensor placement. In a second example, a sample-to-sample transition matrix is established for a data window, and a signal quality index for the transition matrix is determined. In this way, the signal quality index may be determined without relying on motion cancelling or the segmentation of the signal into individual pulse waveform signals. In both examples, signal quality may be confirmed before allowing a data window to contribute to a downstream cardiovascular parameter calculation with a given signal quality index threshold.

FIG. 1 shows aspects of an example sensor-and-logic system in the form of a wearable electronic device 10. The wearable electronic device 10 may be configured to measure, analyze, and/or report one or more health/fitness parameters of a wearer of wearable electronic device 10. Wearable electronic device 10 is not limiting. One or more of the features described below with reference to wearable electronic device 10 may be implemented in another sensor-and-logic system, which optionally may have a form factor that differs from wearable electronic device 10.

Wearable electronic device 10 is shown disassembled in order to depict inner componentry. The illustrated device is band-shaped and may be worn around a wrist. Wearable electronic device 10 includes a primary device 12 and a satellite device 14. Components of primary device 12 and satellite device 14 are indicated by dashed outlines. Primary device 12 may have a form function similar to the main body of a watch, and may comprise the primary user interface componentry (e.g., display, inputs, etc.) for wearable electronic device 10. Satellite device 14 may comprise pulse pressure wave transduction componentry that may enable wearable electronic device 10 to function as a wearable cardiovascular monitoring device. The accuracy of pulse pressure wave transduction may be dependent on the placement of the transduction componentry relative to the wearer's skin and underlying tissue and vasculature. For example, including the pulse pressure wave transduction componentry in satellite device 14 may enable pulse pressure wave transduction at the underside of the wearer's wrist while primary device 12 is situated on the back of the wearer's wrist in a position that is familiar to watch-wearers.

Wearable electronic device 10 is shown having a first strap 16 and a second strap 17. However, in some examples a single strap may be included, and in some examples, more than two straps may be included. The straps of wearable electronic device 10 may be elastomeric in some examples, and one or more of the straps optionally may be comprised of a conductive elastomer. First strap 16 may be connected to primary device 12 at first end 18, while second end 19 is located on the opposite, distal end of first strap 16. Similarly, second strap 17 may be connected to primary device 12 at first end 20, while second end 21 is located on the opposite, distal end of second strap 17. First strap 16 comprises primary fastening componentry 22 located towards second end 19, while second strap 17 comprises secondary fastening componentry 23 located towards second end 21. The straps and fastening componentry enable wearable electronic device 10 to be closed into a loop and to be worn on a wearer's wrist.

In this example, first strap 16 comprises a proximal portion 24 which connects to primary device 12 and a distal portion 25 that comprises primary fastening componentry 22. Proximal portion 24 and distal portion 25 may be coupled together via tertiary fastening componentry 26. In this way the distance between primary device 12 and primary fastening componentry 22 may be adjusted. However, in other examples, first strap 16 may be a single continuous strap that both connects to primary device 12 and comprises primary fastening componentry 22.

Satellite device 14 may be attached to first strap 16 at a fixed position within attachment region 27 of first strap 16, thus establishing a fixed distance between primary device 12 and satellite device 14. Primary fastening componentry 22 and secondary fastening componentry 23 are complementary, and thus may be adjustably engaged to adjust the circumference of wearable electronic device 10 without moving the fixed position of satellite device 14 relative to primary device 12. In this example, primary fastening componentry 22 includes discrete locations for engaging with secondary fastening componentry 23. However, in other examples, primary fastening componentry 22 and secondary fastening componentry 23 may be adjustably engaged along a continuous region.

Wearable electronic device 10 comprises a user-adjacent side 28 and an externally facing side 29. As such, primary device 12, satellite device 14, first strap 16, and second strap 17 may each have a user-adjacent side and externally facing side. In the closed conformation, wearable electronic device 10 thus comprises an inner surface (user-adjacent) and an outer surface (externally facing).

Wearable electronic device 10 includes various functional components integrated into primary device 12. In particular, primary device 12 includes a compute system 32, display 34, communication suite 36, and various sensors. These components draw power from one or more energy-storage cells 39. A battery—e.g., a lithium ion battery—is one type of energy-storage cell suitable for this purpose. Examples of alternative energy-storage cells include super- and ultra-capacitors. In wearable electronic devices worn on the wearer's wrist, the energy-storage cells may be curved to fit the wrist.

In general, energy-storage cells 39 may be replaceable and/or rechargeable. In some examples, recharge power may be provided through a universal serial bus (USB) port, which may include a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the wearer's adventitious or purposeful body motion. For example, batteries or capacitors may be charged via an electromechanical generator integrated into wearable electronic device 10. The generator may be turned by a mechanical armature that turns while the wearer is moving and wearing wearable electronic device 10.

Within primary device 12, compute system 32 is situated below display 34 and operatively coupled to display 34, along with communication suite 36, and various sensors. The compute system 32 includes a data-storage machine 37 to hold data and instructions, and a logic machine 38 to execute the instructions. Aspects of compute system 32 are described in further detail with reference to FIG. 9. These components may be situated within primary device 12 between top device housing frame 40 and bottom device housing frame 42. Primary device 12 may further comprise other actuators that may be utilized to communicate with the wearer, such as haptic motor 44, and/or a loudspeaker (not shown).

Display 34 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, (LCOS) array) may be frontlit via ambient light. A curved display may also be used. Further, active-matrix organic light-emitting diode (AMOLED) displays or quantum dot displays may be used.

Communication suite 36 may include any appropriate wired or wireless communications componentry. In some examples, the communications suite may include a USB port, which may be used for exchanging data between wearable electronic device 10 and other computer systems, as well as providing recharge power. The communication suite may further include two-way Bluetooth, Wi-Fi, cellular, near-field communication and/or other radios. In some implementations, communication suite 36 may include an additional transceiver for optical (e.g., infrared) communication.

In wearable electronic device 10, a touch-screen sensor may be coupled to display 34 and configured to receive touch input from the wearer. The touch-screen sensor may be resistive, capacitive, or optically based. Pushbutton sensors may be used to detect the state of push button 48, which may include rockers. Input from the pushbutton sensor may be used to enact a home-key or on-off feature, control audio volume, turn a microphone on or off, etc.

Wearable electronic device 10 may include a plurality of additional sensors. Such sensors may include one or more microphones, visible-light sensors, ultraviolet sensors, and/or ambient temperature sensors. A microphone may provide input to compute system 32 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

A secondary compute system 50 is located within satellite device 14. Secondary compute system 50 may include a data-storage machine 51 to hold data and instructions, and a logic machine 52 to execute the instructions. Secondary compute system 50 may be situated between top satellite housing frame 54 and bottom satellite housing frame 55. Top satellite housing frame 54 and bottom satellite housing frame 55 may be configured to couple satellite device 14 to a fixed position within attachment region 27 on first strap 16 through the use of screws, bolts, clamps, etc. Top satellite housing frame 54 and bottom satellite housing frame 55 are shown as separate components, but in some examples, they may be coupled together by a hinge on one end, allowing satellite device 14 to be latched together around first strap 16 at the other end.

Secondary compute system 50 may be communicatively coupled to compute system 32. Satellite device 14 may mediate communication between secondary compute system 50 and compute system 32. For example, satellite device 14 may include one or more conductive contacts configured to physically intersect with one or more conductive wires extending from primary device 12 through attachment region 27 within first strap 16. In other examples, secondary compute system 50 may be coupled to compute system 32 via capacitive contact between one or more conductive contacts on satellite device 14 and one or more conductive wires within first strap 16. In other examples, a ribbon cable may extend from primary device 12 through first strap 16 such that one or more contacts on satellite device 14 can intersect with the ribbon cable when the satellite device is affixed to first strap 16. In some examples, secondary compute system 50 may communicate with compute system 32 via wireless communication. In some examples, satellite device 14 may include one or more energy storage cells. In other examples, satellite device 14 and components housed therein may draw power from energy-storage cells 39.

A pressure transducing device 58 is located within satellite device 14. When placed above the wearer's radial artery, the pressure transducing device 58 may transduce a pulse pressure wave present in the radial artery, thus functioning as a radial tonometer. The transduced pulse pressure waves may then be converted into pulse waveform signals and utilized to determine the wearer's heart rate, blood pressure, and other cardiovascular properties. Attachment region 27 may comprise a plurality of possible sensing locations, each possible sensing location having a different effective distance from primary device 12 along the first strap 16. In some examples, attachment region 27 may comprise a plurality of continuous possible sensing locations, while in other examples attachment region 27 may comprise a plurality of discrete possible sensing locations. By adjusting the distance between primary device 12 and satellite device 14, satellite device 14 and pressure transducing device 58 may be placed directly over the wearer's radial artery while primary device 12 is positioned on the back of the wearer's wrist. In some examples, satellite device 14 may be coupled to first strap 16 at a fixed position (e.g., at second end 19). In such examples, the distance between satellite device 14 and primary device 12 may be adjusted via interactions between satellite device 14 and first strap 16, via interactions between first strap 16 and primary device 12, and/or between regions of first strap 16.

Bottom satellite housing frame 55 is shown with an opening through which pressure transducing device 58 can establish contact with the wearer's wrist at the radial artery. Wearable electronic device 10 may be configured to instruct the wearer to adjust the position of satellite device 14 relative to the radial artery if a pressure detected by the pressure transducing device 58 is below a threshold, and/or if a signal quality of the transduced pressure is below a threshold. In some examples, wearable electronic device 10 may be configured to self-adjust the position of satellite device 14 and/or the overall circumference of wearable electronic device 10.

In some examples, pressure transducing device 58 may be housed and configured to interface with a wearer's wrist independently from primary device 12. For example, pressure transducing device 58 may be worn on one wrist, while primary device 12 may be worn on the other wrist. In other examples, pressure transducing device 58 may be configured to be worn while primary device 12 is not worn. Pressure transducing device 58 may thus be configured to communicate with one or more additional computing devices, (e.g., via secondary compute system 50) such as a personal computer, tablet computer, smart phone, smart watch, gaming device, etc.

FIG. 1 shows a pair of contact sensor modules 60 and 61 situated on top device housing frame 40, which may be touchable by a wearer using fingers on the hand opposite the wrist where wearable electronic device 10 is worn. In some examples, other contact sensor modules may be included in addition to or as an alternative to contact sensor modules 60 and 61. As one example, other contact modules may be attached to user-adjacent side 28 of primary device 12, first strap 16 and/or second strap 17, and thus be held in contact with points on the wearer's wrist when wearable electronic device 10 is worn. As another example, one or more contact modules may be situated at or near secondary fastening componentry 23 on the externally-facing side 29 of wearable electronic device 10 when wearable electronic device 10 is closed into a loop, thus allowing the wearer to contact a point on their body reachable with the underside of the wearer's wrist. Additionally or alternatively, one or more contact modules may be situated on the externally-facing side 29 of the loop at first strap 16 and/or second strap 17.

Contact sensor modules 60 and 61 may include independent or cooperating sensor elements, to provide a plurality of sensory functions. For example, contact sensor modules 60 and 61 may provide an electrical resistance and/or capacitance sensory function, which measures the electrical resistance and/or capacitance of the wearer's skin. Compute system 32 may use such input to assess whether or not the device is being worn, for instance. In some implementations, the sensory function may be used to determine how tightly wearable electronic device 10 is being worn. In some examples, a contact sensor module may also provide measurement of the wearer's skin temperature. In some examples, contacting multiple contact sensor modules may allow compute system 32 to determine an electrocardiogram (EKG) of the wearer.

Wearable electronic device 10 may also include motion sensing componentry, such as an accelerometer, gyroscope, and magnetometer. The accelerometer and gyroscope may furnish acceleration data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The wearable electronic device may also include a global positioning system (GPS) receiver for determining the wearer's geographic location and/or velocity. In some configurations, the antenna of the GPS receiver may be relatively flexible and extend into straps 16 and/or 17. In some examples, data from the motion sensing componentry may be utilized to determine a position of the wearable electronic device 10, contact modules 60 and or 61, and/or pressure transducing device 58 relative to predetermined sensing locations on the body of the device wearer.

In some examples, wearable electronic device 10 may also include one or more optical sensors paired with one or more optical sources. The optical sources may be configured to illuminate the skin and/or the underlying tissue and blood vessels of the wearer, while the optical sensors may be configured to detect illumination reflected off of the skin and/or the underlying tissue and blood vessels of the wearer. This optical data may be communicated to compute system 32, where the data may be used to determine the wearer's blood-oxygen level, pulse, blood glucose levels, or other biometric markers with optical signatures.

Compute system 32, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

Figure 2:
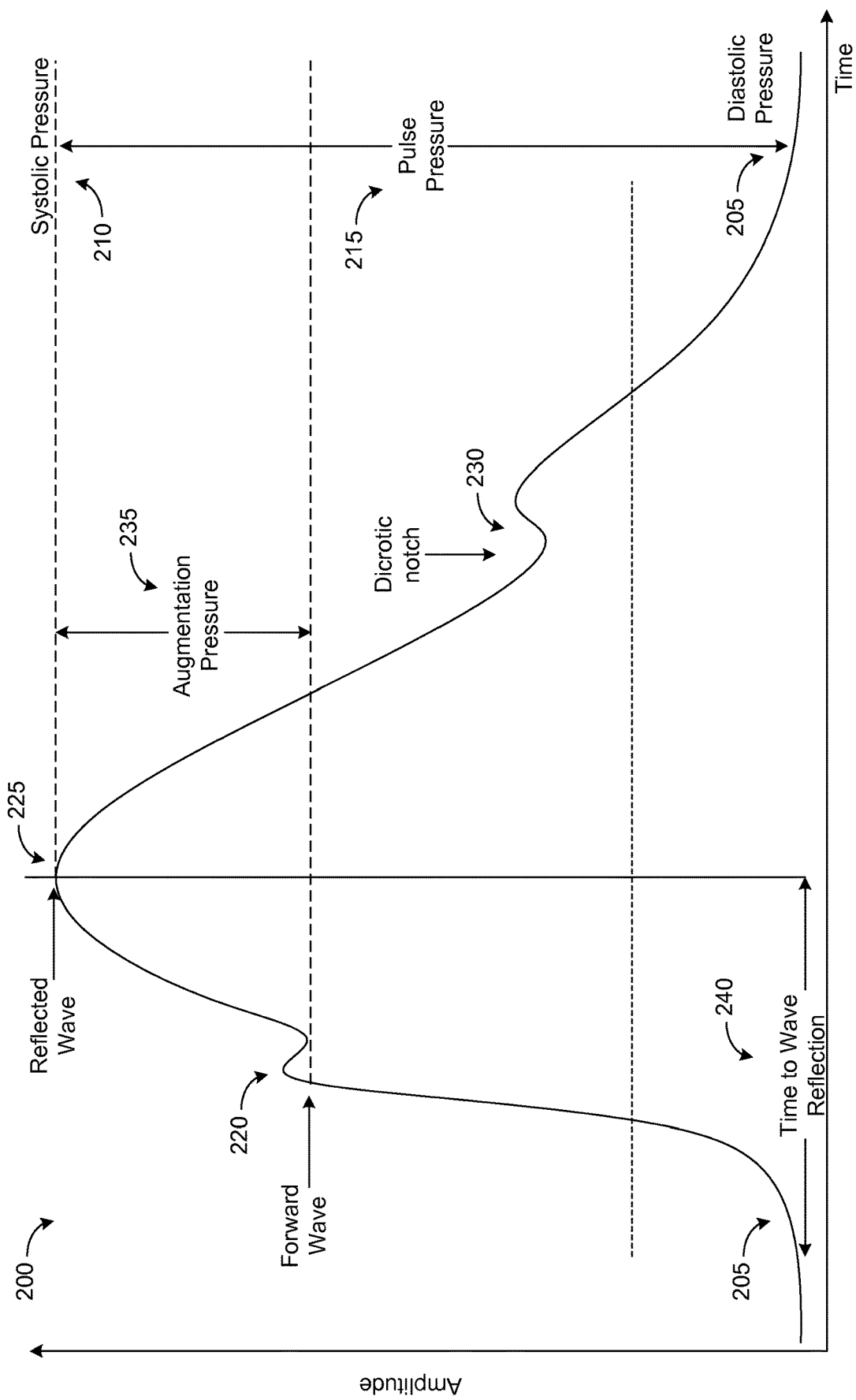
FIG. 2 shows an example pulse waveform signal.

FIG. 2 shows an illustration of an exemplary pulse waveform signal 200 depicting how the pressure in a radial artery changes over the course of a single heartbeat, or cardiac cycle. A cardiac cycle consists of two primary periods: diastole and systole. During diastole, the ventricular musculature is relaxed, and the blood pressure in the outlying vasculature, such as the radial artery, is low, as indicated at 205 (diastolic pressure). During systole, the ventricular musculature contracts, forcing blood into the vasculature, which increases the vascular blood pressure up to a maximum value, known as the systolic pressure, as indicated at 210. For a low resolution or low-quality signal (low signal-to-noise ratio), the general, periodic wave form of the pulse may be identifiable. A pulse rate may be calculated based on the frequency of peaks and troughs (and/or zero-crossing events) within the pulse waveform signal, and then the pulse pressure 215 may be calculated based on the amplitude of the pulse waveform signal. In some examples, the systolic and diastolic pressures may be calculated.

While these physiological parameters are clinically relevant, they have limited use in determining the overall cardiovascular health of an individual. Given pulse waveform signal with a high resolution and high quality, additional useful information may be extracted and used to develop a more complete model of an individual's cardiovascular health. The periodicity of the pulse waveform signal allows for a significant number of data points to be accumulated in a relatively short period of time, thus enabling the extraction of pulse waveform signal characteristics with significant clinical importance.

The forward wave, indicated at 220, represents the pulse wave generated by the heart contracting. The reflected wave, indicated at 225, represents the pulse wave reflecting back to the heart. The dicrotic notch, shown at 230, is a small increase in blood pressure which occurs when ventricular blood pressure drops and the semilunar valves close. The physical motion of the aortic valve closing creates a small pulse which travels through the radial artery and registers as a pressure increase.

The difference in magnitude between the forward wave pressure and total systolic pressure is known as the augmentation pressure, as indicated at 235. The augmentation pressure and pulse pressure can be used to calculate a value known as the augmentation index, which is frequently used as an indicator of cardiovascular health, particularly as it applies to arterial stiffness.

The duration between the beginning of systole (wherein the radial artery pressure begins to increase) and the arrival of the reflected wave is indicated at 240 as the time to wave reflection. This value is inversely proportional to arterial stiffness. Highly elastic (healthy) blood vessels take longer to reflect a pulse wave, while stiff blood vessels reflect the pulse quickly. In an individual with stiff arteries, the time to wave reflection will be reduced and the reflected wave will arrive at the radial artery much closer to the forward wave. As such, the two waves will combine to a greater extent, and result in a much sharper pressure "peak" observable on the waveform. As the time to wave reflection decreases, the systolic pressure increases, as less of the forward wave's pressure dissipates by the time it combines with the reflected wave.

Pulse waveform signals with high signal quality, such as pulse waveform signal 200, can therefore be very clinically useful, as they allow a clinician to approximately determine a patient's arterial stiffness. In practice, the parameters defining signal quality are application-dependent. Features relevant to successful estimation of signal quality may change depending on what physiological parameters are going to be extracted from the signal downstream in the processing pipeline. Similarly, thresholds for minimum allowable signal quality may also change. As described with reference to pulse waveform signal 200, a relatively low signal quality may be adequate for basic parameters, such as heart rate. More descriptive parameters, such as augmentation pressure and time to wave reflection, may require a higher signal quality in order for the relevant pulse pressure wave features to be extracted and quantified. As such, determining the signal quality of a pulse waveform signal is an important initial step for a heart monitoring device.

Figure 3:
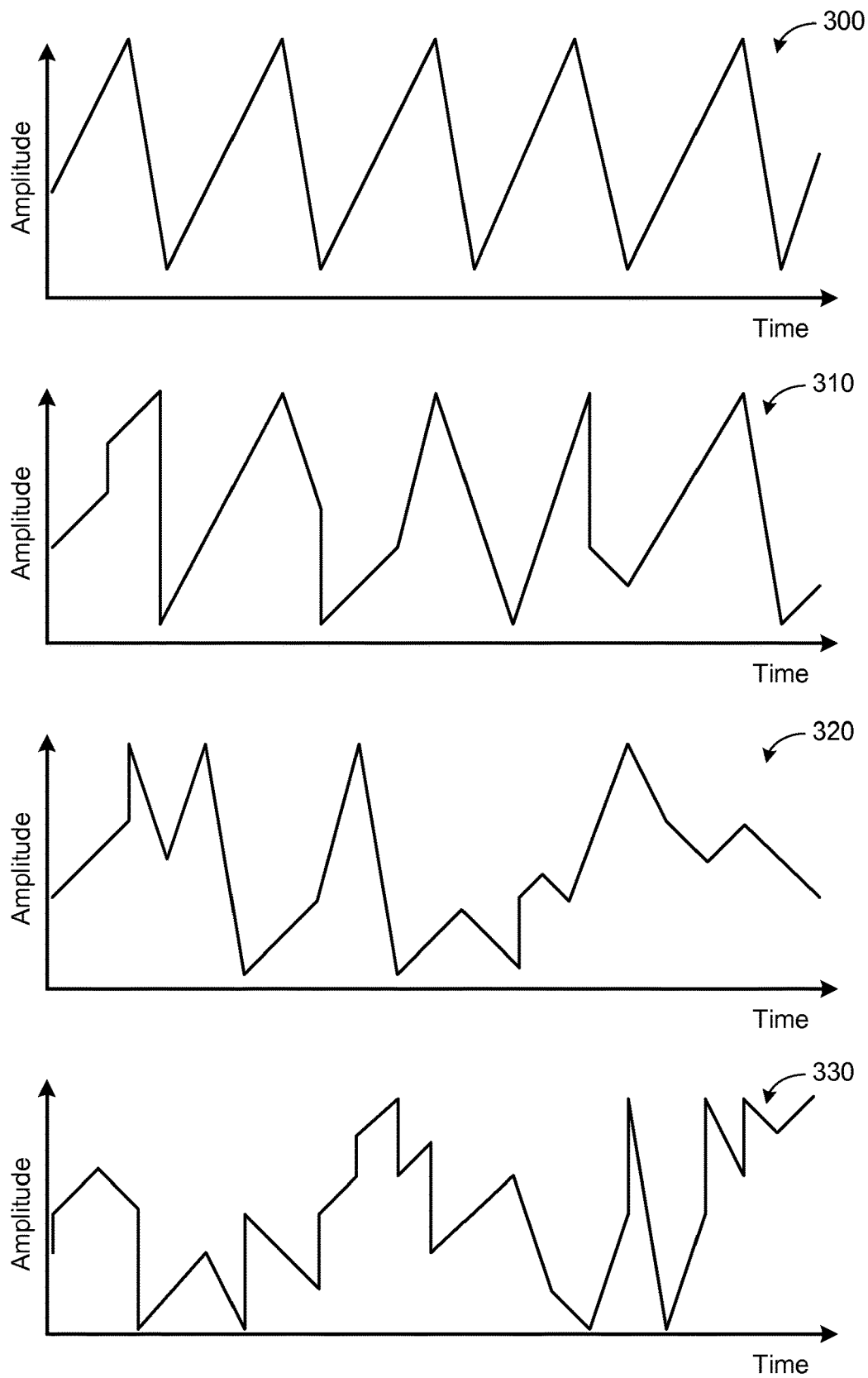
FIG. 3 shows example pulse waveform signals of varying signal quality.

FIG. 3 shows four examples of signal quality for a seven-second window of a photoplethysmogram (PPG) signal (e.g., received from an optical pulse sensing device). Plot 300 includes a pulse waveform signal of excellent signal quality, wherein all beats can be easily visually identified. Plot 310 includes a pulse waveform signal of good signal quality, wherein more than half of beats, but not all beats can be visually identified. Plot 320 includes a pulse waveform signal of mediocre signal quality, wherein fewer than half, but more than one beat can be visually identified. Finally, plot 330 includes a pulse waveform signal of poor signal quality, wherein one or fewer beats can be visually identified. In these examples, the pulse waveform signal is entirely preserved in plot 300, and is preserved to lessening degrees as signal quality decreases.

While the raw pulse waveform signal can be manipulated and conditioned to remove noise artifacts, incorrect or inconsistent sensor placement cannot be overcome by mere data processing. Both optical and pressure based sensors require correct sensor placement in order to output a signal representative of the pulse waveform signal, regardless of signal resolution. For example, a radial tonometer, such as satellite device 14 shown in FIG. 1, needs to be placed directly above the radial artery, between the radius and the flexor carpi radialis tendon, in order for radial artery pressure changes to be conducted to a pressure sensor within the tonometer. The signal quality of the pulse waveform signal may be leveraged to augment initial sensor positioning by providing user feedback indicative of confidence that the sensor is placed in the correct sensor position.

For individuals using a wearable heart monitoring device who do not have clinical experience, this feedback may decrease the time needed to correctly place the sensor, leading to a more pleasing user experience. Over time, a user may thus learn proper positioning based on the positional feedback, further decreasing placement time. Correct sensor placement will increase the quality of pulse waveform signals, thereby allowing for the calculation of more accurate and more precise cardiovascular parameters.

In order to help a user quickly place the sensor in a sensor location, a classifier cascade may be utilized to progressively determine signal quality. The classifier cascade may be organized such that an initial classifier with a low false-negative rate (high signal acceptance rate) is applied to an initial data window. In this way, some low-quality signals are rejected without falsely rejecting high-quality signals. If the signal is accepted, a larger window of data is subjected to a classifier with a lower false-positive rate (higher signal rejection rate). This process may be repeated with increasingly precise classifiers at each stage. If a signal is rejected, the cascade begins anew at the initial classifier with a new initial data window. In this way, the classifier cascade vets good signals with increasing confidence at each successive classifier.

Figure 4:
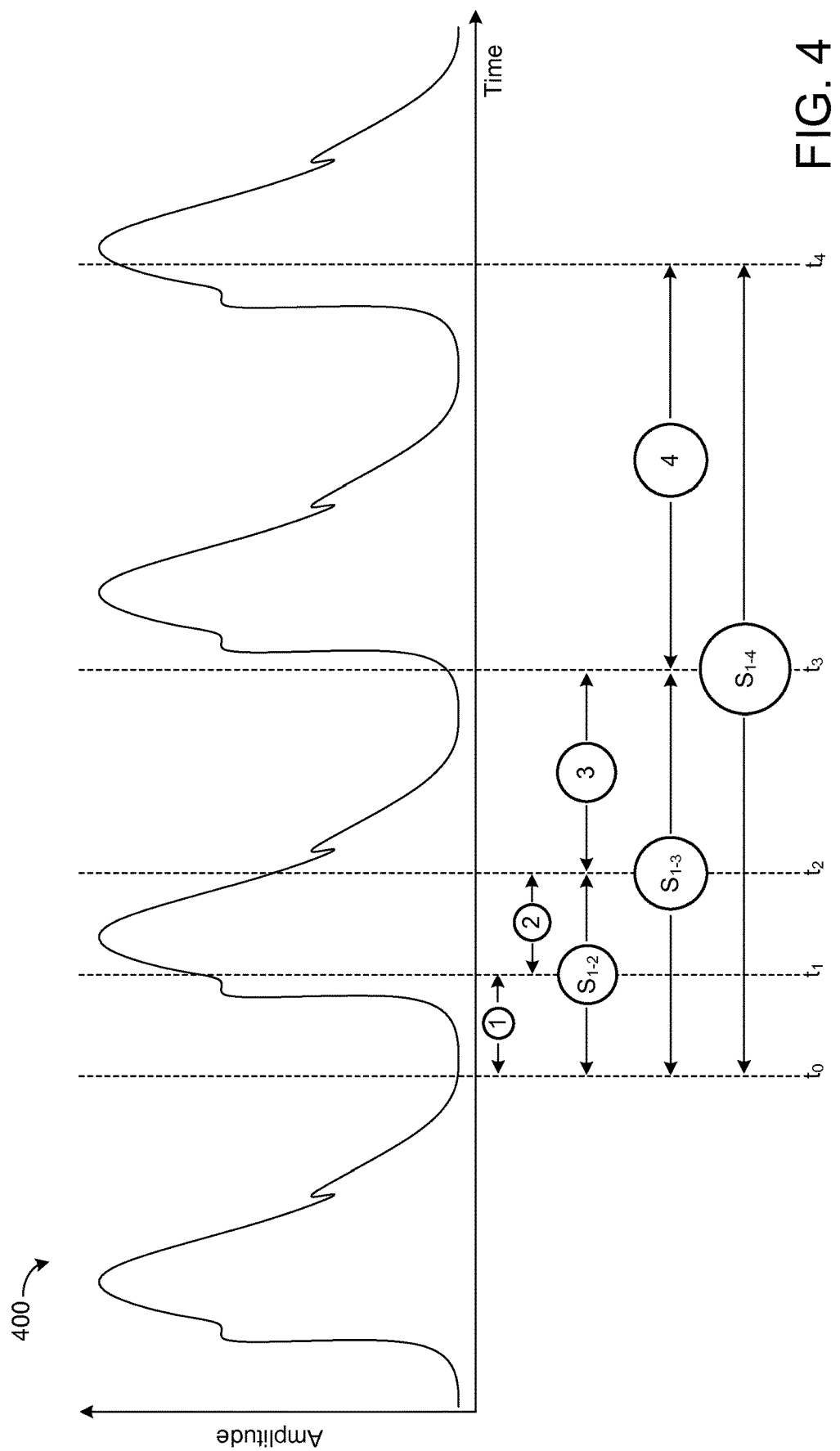
FIG. 4 shows an example pulse waveform signal divided into windows of increasing length.

FIG. 4 shows an example pulse pressure signal 400, illustrated as a pressure (amplitude) over time, while FIG. 5A shows a flow chart for an example classifier cascade. The pulse pressure signal may comprise a plurality of samples, and may be divided into windows of various lengths, the data windows comprising a number of samples proportionate to the length of the data window. The data windows (1), (2), (3), and (4) may have increasing lengths. For example, data window (1) may represent 0.25 seconds of pulse pressure signal 400, data window (2) may represent 0.5 seconds of the pulse pressure signal, data window (3) may represent 1 second of pulse pressure signal, and data window (4) may represent 2 seconds of pulse pressure signal. In this example, the classifier cascade comprises four classifiers ($C_1$, $C_2$, $C_3$, and $C_4$), but more or fewer classifiers may be used in other examples. Further, the length and number of windows, and/or the number and stringency of classifiers may be varied over time to improve accuracy and/or for providing user feedback.

The classifier cascade may be trained through machine-learning to identify pulse waveform signals, and may further be trained to recognize signal features that are characteristic of pulse waveform signals of varying quality. The classifier cascade may be trained to extract one or more signal features from a pulse waveform signal window, and may further be trained to assign a signal quality index (SQI) to a pulse waveform signal window based on the one or more extracted signal features.

Signal features may include, but are not limited to, a slope of a linear signal model (i.e., the value of the slope [a] after fitting a linear model [a]t+[b] to the signal window); the maximum non-initial autocorrelation peak (where peaks may be defined as any index [t] such that x[t−1]<x[t] and x[t+1]<x[t]); the number of autocorrelation peaks; the signal standard deviation; the peak to peak amplitude (max-min) of the signal; the spectral energy ratio (high frequencies to low frequencies, where the sum of the absolute values of the values in the upper half of the spectrum are divided by the same for the lower half); the number of signal peaks; the location of first (non-initial) peak in autocorrelation; and/or the mean amplitude of the original signal. All of the cited features aside from the slope and mean value may be computed from the mean subtracted, linear-corrected signal window. Classifier features may additionally include the presence or absence of known morphological landmarks in the pressure waveform, such as those shown in FIG. 2.

The same set of features may be used in every stage of the cascade, or different sets of features may be used. Similarly, while all of the signal features referred to are of the same type and may be combined through gradient-boosted mixtures of decision trees in the machine-learning process, other types of features may be used in addition to or as an alternative to those listed. In the context of real-time, interactive signal quality estimation, more time and computational effort may be used on longer data windows than on shorter, initial data windows. Thus, more complex features may be used for downstream classifiers, while less complex features may be used for initial classifiers. For example, more complex feature families which may utilize additional computational resources, such as spectral, wavelet, and/or autoregressive features may be used, and/or the same feature families may be used with additional parameters (e.g., a mixture of a larger number of trees and/or deeper trees).

Once the classifiers have been trained, the cascade is run as is shown by flowchart 500 in FIG. 5A. The signal fed to the classifier cascade may be raw or pre-processed. For example, the signal may be passed through one or more filters, such as a bandpass or motion filter, may be passed through an initial vetting stage to ensure the pulse waveform signal comprises an initial signal characteristic, may be divided into data windows (overlapping and/or non-overlapping), etc. prior to any data being provided to the initial classifier.

In this example, a first data window (1) is provided to the first classifier $C_1$. Classifier $C_1$ is used to determine whether data window (1) meets a threshold that is representative of correct pulse sensing device placement. The threshold for classifier $C_1$ may be selected at a point approaching a 100% true-positive rate, but with a potentially high false-positive rate, as shown by the sample receiver operating characteristic (ROC) curve 501 and threshold selection ($T_1$) for classifier $C_1$ depicted in FIG. 5B. If data window (1) does not meet threshold $T_1$, the data window is rejected, and a new, subsequent data window (1) is provided to Classifier $C_1$.

If data window (1) does meet threshold $T_1$, subsequent samples are added to the data window until data window (2) is fully received from the pulse sensing device. The concatenated window ($S_{1-2}$) comprises the samples for both data window (1) and data window (2). Concatenated window ($S_{1-2}$) is then provided to second classifier $C_2$. The threshold for classifier $C_2$ may also be selected at a point approaching a 100% true-positive rate, but with a lower false-positive rate than for classifier $C_1$, as shown by the sample receiver operating characteristic (ROC) curve 502 and threshold selection ($T_2$) for classifier $C_2$ depicted in FIG. 5C. If concatenated window ($S_{1-2}$) does not meet threshold $T_2$, the data window is rejected, and a new, subsequent data window (1) is provided to classifier $C_1$.

If concatenated window ($S_{1-2}$) does meet threshold $T_2$, subsequent samples are added to the data window until data window (3) is fully received from the pulse sensing device. Concatenated window ($S_{1-3}$) thus comprises the samples for data windows (1), (2), and (3), and is provided to classifier $C_3$. Classifier $C_3$ also may have a true-positive rate approaching 100%, but with a lower false positive rate than for classifier $C_2$. If concatenated window ($S_{1-3}$) does not meet the threshold for classifier $C_3$, the data window is rejected, and a new, subsequent data window (1) is provided to classifier $C_1$.

If concatenated window ($S_{1-3}$) does meet the threshold for classifier $C_3$, subsequent samples are added to the data window until data window (4) is fully received from the pulse sensing device. Concatenated window ($S_{1-4}$) thus comprises the samples for data windows (1), (2), (3), and (4), and is provided to classifier $C_4$. Classifier $C_4$ also may have a true-positive rate approaching 100%, but with a lower false positive rate than for classifier $C_3$. If concatenated window ($S_{1-4}$) does not meet the threshold for classifier $C_4$, the data window is rejected, and a new, subsequent data window (1) is provided to classifier $C_1$. If concatenated window ($S_{1-4}$) does meet the threshold for classifier $C_4$, concatenated window ($S_{1-4}$) is accepted, and the pulse waveform signal may be used in downstream calculations of cardiovascular parameters.

An advantage of using cascading classifiers with regard to pulse detection is that there is a reduced latency on returned data. This may enable an interactive feature for providing user feedback. For example, as a user attempts to place a pulse pressure sensor in place over the radial artery, initial rapid classifiers may indicate whether the signal is good or bad. This feedback may be given to the user to augment sensor placement, by indicating if the sensor needs to be moved significantly (bad signal), slightly (moderate quality signal), or not at all (good signal). Gradients of feedback may be used to indicate if the signal quality is improving or declining.

Figure 6:
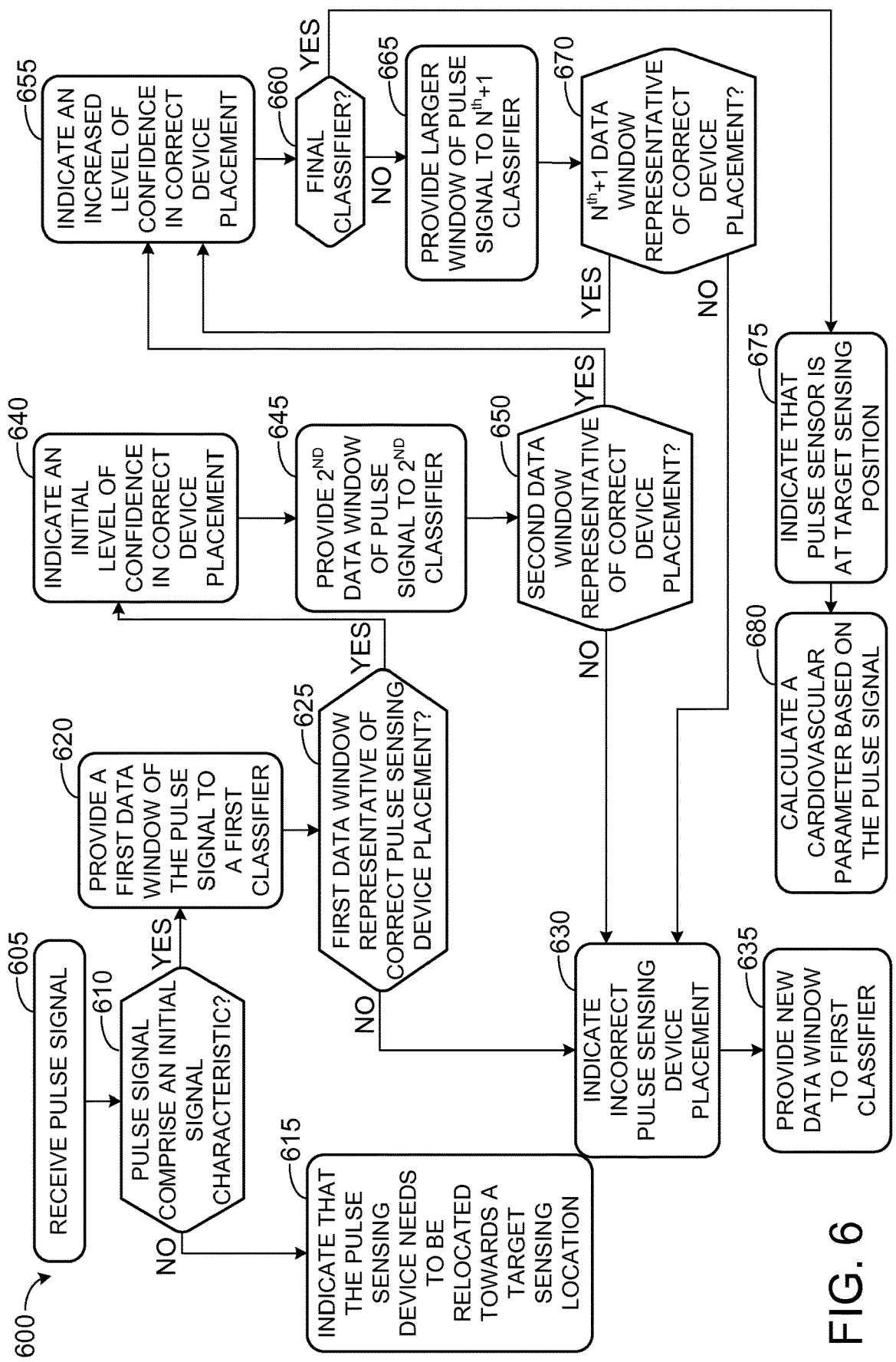
FIG. 6 shows a flow chart for an example method of providing user feedback regarding placement of a pulse sensing device.

FIG. 6 shows a flow chart for an example method 600 of providing user feedback regarding placement of a pulse sensing device using a classifier cascade, such as the classifier cascade depicted in FIG. 5A. Method 600 may be applied to a wearable cardiovascular monitoring device. In this example, user feedback will be described in terms of visual cues provided by a feedback machine, for example, a display device or set of LEDs at the wearable cardiovascular monitoring device. However, other forms of user feedback may be provided through one or more feedback machines, such as audio cues, haptic cues, combinations of cues, etc. and/or different forms of user feedback may be provided at different stages of progression through the classifier cascade.

At 605, method 600 includes receiving a pulse waveform signal from a pulse sensing device. For example, a pulse waveform signal may be received from an optical pulse sensing device, an arterial tonometer, etc. The pulse waveform signal may be pre-processed prior to being received. For example, one or more filters may be applied to a raw pulse waveform signal received directly from the pulse sensing device.

At 610, method 600 includes computer-determining whether the pulse waveform signal comprises an initial signal characteristic. For example, an initial signal characteristic may include a periodicity or amplitude representative of a pulse waveform signal. In this way, the absence of a pulse waveform signal can be identified, distinguished from a low-quality pulse waveform signal, and appropriate user-feedback can be provided.

If the pulse waveform signal does not comprise the initial signal characteristic, method 600 proceeds to 615. At 615, method 600 includes providing user feedback indicating that the pulse sensing device needs to be relocated towards a target sensing location. For example a flashing red signal may be output via the feedback machine.

If the pulse waveform signal does comprise the initial signal characteristic, method 600 proceeds to 620, and includes providing a first data window, comprising a first number of samples, of the pulse waveform signal to a first classifier. At 625, method 600 includes computer-analyzing the first data window of the pulse waveform signal to determine whether the first data window is representative of correct pulse sensing device placement. For example, a signal quality index of the first data window may be determined based on one or more signal characteristics of the data window, and then compared to a first threshold. If it is determined that the first data window does not indicate correct pulse sensing device placement, method 600 proceeds to 630, and includes providing user feedback indicating incorrect pulse sensing device placement. For example, an unblinking red light may be output via the feedback machine. Continuing at 635, method 600 includes providing a new data window of the pulse waveform signal, comprising the first number of samples, to the first classifier. The new data window may then be computer analyzed with the first classifier, and the method may then continue as described.

If it is determined that the first data window does indicate correct pulse sensing device placement, method 600 proceeds to 640, and includes providing user feedback indicating an initial level of confidence that the pulse sensing device is correctly placed. For example, a flashing yellow light may be output via the feedback machine. Continuing at 645, method 600 includes providing a second data window of the pulse waveform signal, comprising a second number of samples, to a second classifier. As described with reference to FIGS. 4 and 5A, the second data window may comprise a second number of samples larger than the first number of samples, and the samples in the second data window may include all of the samples in the first data window. Further, the second classifier may have a lower false-positive rate than the first classifier.

Continuing at 650, method 600 includes computer-analyzing the second data window of the pulse waveform signal to determine whether the first data window is representative of correct pulse sensing device placement. If it is determined that the second data window does not indicate correct pulse sensing device placement, method 600 proceeds to 630, and includes providing user feedback indicating incorrect pulse sensing device placement, such as an unblinking red light. Continuing at 635, method 600 includes providing a new data window of the pulse waveform signal, comprising the first number of samples, to the first classifier, as described.

If it is determined that the second data window does indicate correct pulse sensing device placement, method 600 proceeds to 655, and includes providing user feedback indicating an increased level of confidence that the pulse sensing device is correctly placed. For example, the flashing yellow light may be output via the feedback machine with an increased flashing frequency. Continuing at 660, method 600 includes determining whether the current data window has been computer-analyzed by a final classifier in the classifier cascade. If the current data window has not been computer-analyzed by a final classifier, method 600 proceeds to 665, and includes providing an $N+1^{st}$ window of the pulse waveform signal to an $N+1^{st}$ classifier. For example, following the second classifier, a third data window may comprise a third number of samples, larger than the second number of samples, and the samples in the third data window may include all of the samples in the second data window (including all of the samples in the first data window). Further, the third classifier may have a lower false-positive rate than the second classifier. Continuing at 670, if it is determined that the $N+1^{st}$ data window does not indicate correct pulse sensing device placement, method 600 proceeds to 630, and includes providing user feedback indicating incorrect pulse sensing device placement. However, if it is determined that the $N+1^{st}$ data window does indicate correct pulse sensing device placement, method 600 returns to 655, and includes providing user feedback indicating an increased level of confidence that the pulse sensing device is correctly placed (e.g., increasing the frequency of the flashing yellow light). Returning to 600, if the current data window has not been computer-analyzed by a final classifier, method 600 includes providing sequentially larger data windows of the pulse waveform signal to increasingly stringent classifiers.

When computer-analysis of the final data window indicates correct pulse sensing device placement, method 600 proceeds to 675, and includes providing user feedback indicating that the pulse sensing device is correctly placed at the target sensing location. For example an unblinking green light may be output via the feedback machine. Continuing at 680, method 600 includes computer-calculating a cardiovascular parameter based on the pulse waveform signal, such as a heart rate, or other parameters described herein.

Most approaches for mitigating motion artifacts in a pulse pressure waveform signal rely on filtering a motion signal from the pulse waveform signal. However, for ambulatory motion, which has a similar frequency spectrum to heart rate, this may also result in filtering the actual pulse pressure wave from the pulse waveform signal, leaving only artifact. Other methods for determining signal quality in a pulse waveform signal comprise segmenting a pulse waveform signal into individual pulse pressure waves, then comparing each individual pulse waveform signal to a template. However, these methods rely on successfully segmenting a pulse waveform signal, which is not always reliable when the artifact to be identified is similar (quasi-periodic with a similar fundamental frequency) to the pulse waveform signal of interest. Further, many of these algorithms use the derivative of the waveform for beat segmentation. Signal quality may then be estimated leveraging the fact that beat morphology is fairly consistent over short periods. As such, these methods are susceptible to falsely developing a self-reinforcing model of pulse morphology that is based solely on motion-induced waveform changes.

Figure 7:
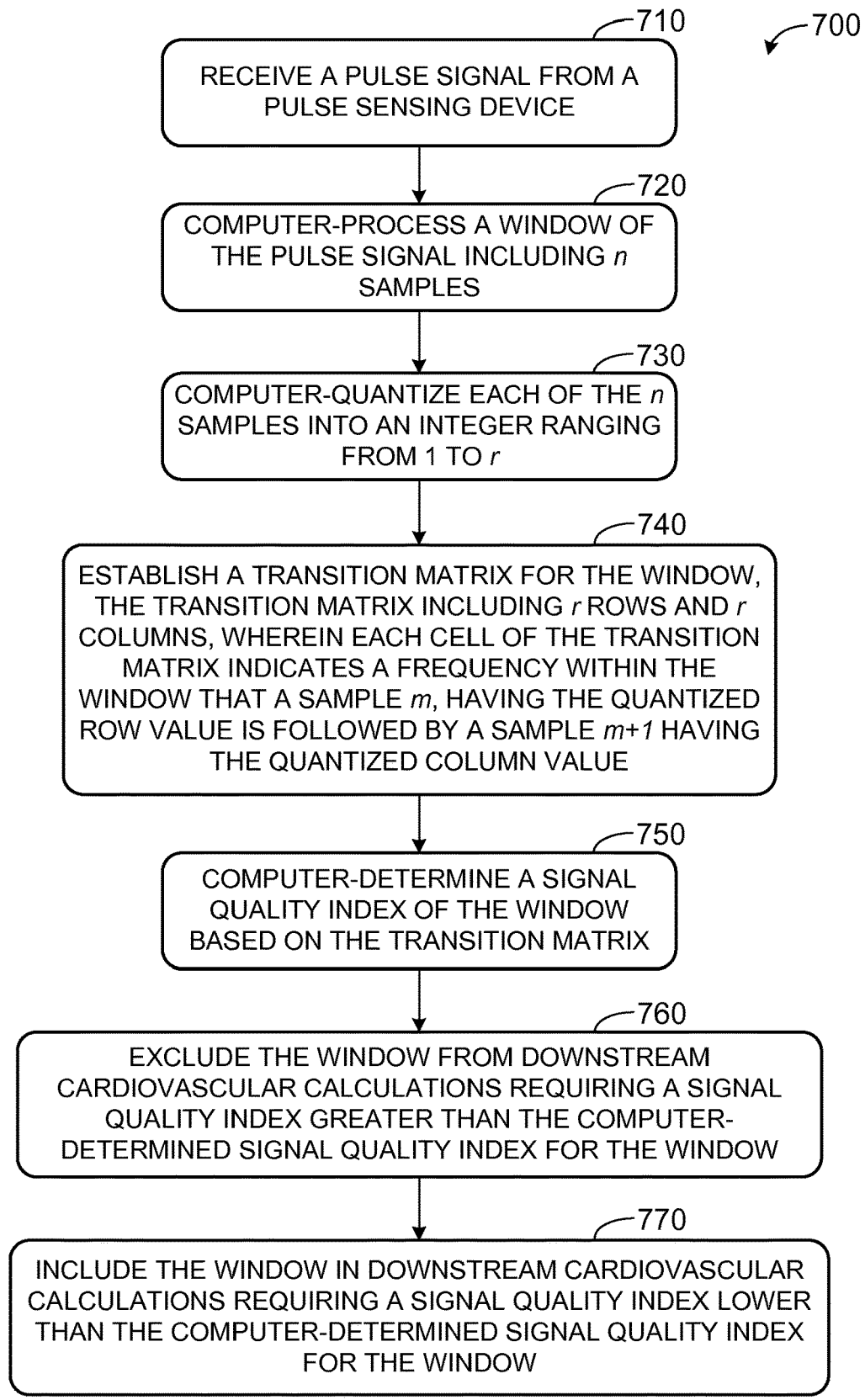
FIG. 7 shows a flow chart for an example method of estimating signal quality using a sample-to-sample transition matrix.

FIG. 7 shows a flow chart for an example method 700 enabling signal quality estimation without motion filtering, and without beat segmentation. The method is applicable to wearable cardiovascular monitors worn by individuals who are standing, running, walking, or performing other ambulatory tasks. Method 700 utilizes the quasi-periodic, highly stereotyped nature of the pulse waveform signal without the need for beat segmentation, and may be applied to pulse waveform signals received from a variety of pulse sensing devices, including optical sensors and tonometers.

At 710, method 700 includes receiving a pulse waveform signal from a pulse sensing device. For example, a pulse waveform signal may be received from an optical pulse sensing device, an arterial tonometer, etc. At 720, method 700 includes computer-processing a window of the pulse waveform signal including n samples. The received pulse waveform signal may be a raw pulse waveform signal or a pre-processed pulse waveform signal. To derive a pre-processed signal from a raw signal, the pulse waveform signal may be computer processed by being subjected to one or more filters, such as a band pass filter (e.g., a zero-phase digital filter such as a 4th order Butterworth where, $F_{LP}$=0.5 Hz, and $F_{HP}$=50 Hz). In this example, the raw pulse waveform signal is not subject to motion filtering. Following filtering, the pulse waveform signal may be downsampled and divided into windows. As an example, the pulse waveform signal may be divided into seven-second non-overlapping windows. The raw pulse waveform signal may be acquired at a high sampling rate, such that a window includes a number of samples greater than n. In one example, a 1000 Hz pulse waveform signal may be downsampled to 15 Hz. For a resulting 7 second window, n would thus equal 105 samples.

At 730, method 700 includes computer-quantizing each of the n samples of the data window into an integer ranging from 1 to r. Prior to computer-quantizing the n samples, the data window may be locally normalized, for example on the interval [0, 1]. The value of r is based on a bit depth selected for quantization. For example, a selected bit depth of 4 yields a possible 16 integer values. Each of the n samples within the window may then be assigned one of the discrete values ranging from 1 to 16 (or one of the discrete values ranging from 0000 to 1111 in binary).

At 740, method 700 includes establishing a transition matrix for the window. The transition matrix may include r rows and r columns. Each cell of the transition matrix may indicate a frequency within the window that a sample m, having the quantized row value is sequentially followed in the data window by a sample m+1 having the quantized column value. For example, the cell [1, 1] indicates a frequency that a sample m (e.g., the $42^{nd}$ sample in the downsampled window) having a value of 1 is sequentially followed in the data window by a sample m+1 (e.g., the $43^{rd}$ sample in the downsampled window) also having a value of 1. As another example, the cell [1, 2] indicates a frequency that a sample m having a value of 1 is sequentially followed in the data window by a sample m+1 having a value of 2. The transition matrix may then be normalized to yield the probability distribution $p(x_{n+1}|x_n)$.

Figure 8:
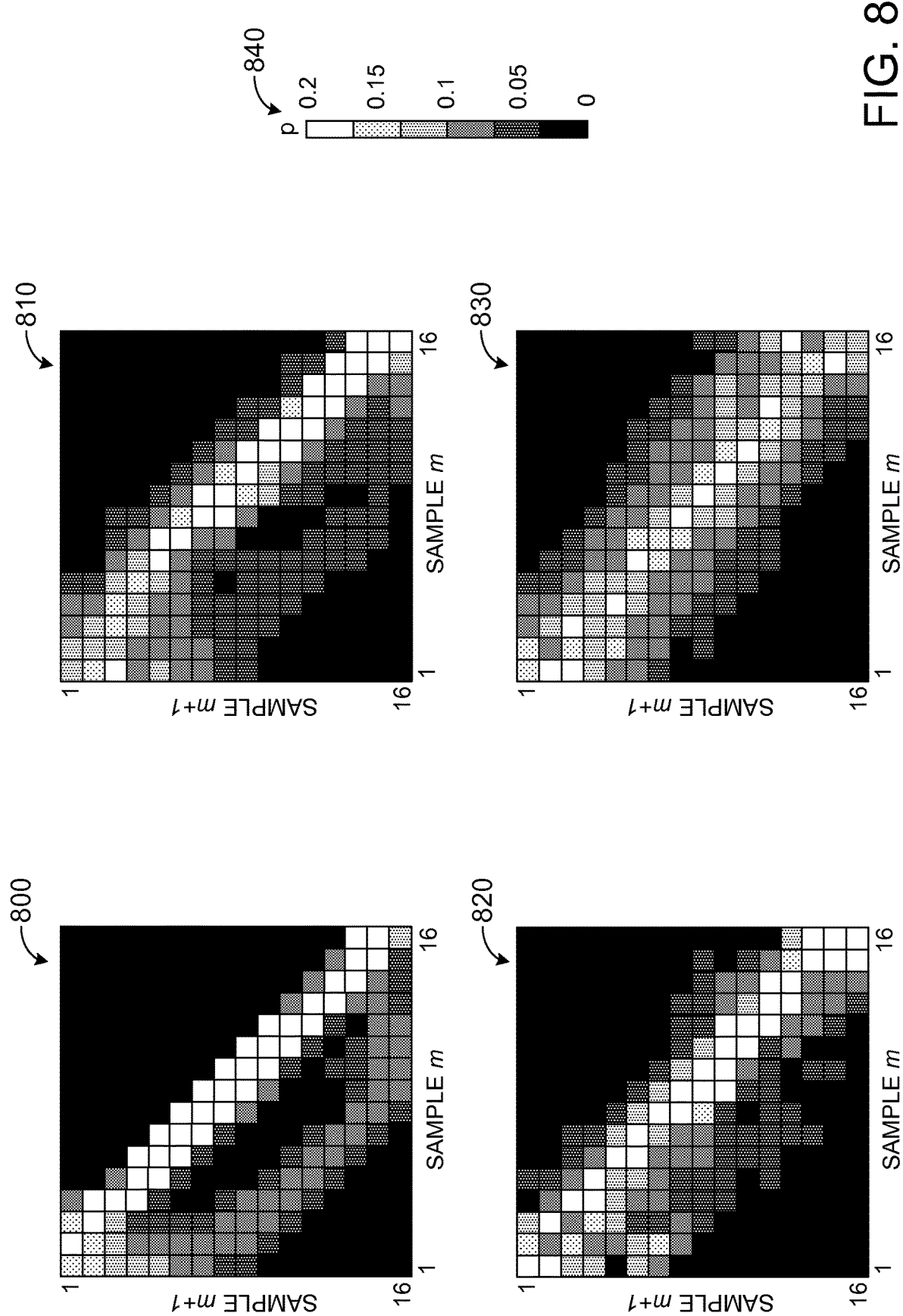
FIG. 8 shows example sample-to-sample transition matrices for pulse waveform signals of varying quality.

FIG. 8 shows example sample-to-sample transition matrices for four data windows of varying signal quality. Using the same rating system applied to the pulse waveform signals shown in to FIG. 3, matrix 800 is derived from a pulse waveform signal of excellent signal quality, matrix 810 is derived from a pulse waveform signal of good signal quality, matrix 820 is derived from a pulse waveform signal of mediocre signal quality, and matrix 830 is derived from a pulse waveform signal of poor signal quality. As shown in legend 840, lighter cells represent higher probabilities, while darker cells represent lower probabilities. In this example, the probabilities have been truncated above p=0.20, in order to enhance the visibility of off-diagonal components.

Qualitative differences may be observed between the matrices derived from higher quality pulse waveform signals and lower quality pulse waveform signals. The pulse waveform signal is intrinsically asymmetric, as can be seen for matrix 800. Further, in a high-quality signal, the highest probabilities lie on the diagonal, as m+1 is likely to be similar to m. As the signal quality decreases, the matrices become more symmetric, and the sample-to-sample transition probability becomes more broadly and more randomly dispersed throughout the matrix (e.g., matrix 830). Motion signals are quasi-periodic, and thus increasing signal contamination from motion artifacts is observable.

Returning to FIG. 7, at 750, method 700 includes computer-determining a signal quality index of the window based on the transition matrix. A classifier may be trained via machine learning, in similar fashion to the classifier training discussed with reference to FIGS. 4-6. As this feature subset is highly dimensional in nature (256 features) an example method for classifying may include the employment of a late fusion approach with a linear support vector machine (SVM) trained for regression (SVR) on the sample-to-sample transition matrices using signal quality indexes as labels. In one example, the SVM may be implemented using L2-loss regularization. The prediction output of the SVR may then be fused with the remaining feature set for signal quality prediction. In each fold, the SVR may be trained on training data alone, but features may be extracted for all training and test data to allow for training of a $2^{nd}$-stage ML algorithm.

Continuing at 760, method 700 includes excluding the data window from downstream cardiovascular parameter calculations requiring a signal quality index greater than the computer-determined signal quality index for the window. At 770, method 700 includes including the data window in downstream cardiovascular parameter calculations requiring a signal quality index lower than the computer-determined signal quality index for the window. As different parameters may require different signal qualities, a good-but-not-excellent data window, such as the data window represented by matrix 810 may be adequate for calculating parameters such as heart rate, but inadequate for calculating parameters such as augmentation pressure.

In some examples, the sample-to-sample transition matrices may be combined with other signal quality features to produce a combined signal quality index. When fused with features that are sensitive to discrete motion events (e.g., autocorrelation metrics), both periodic and aperiodic signal contaminants may be robustly identified. For example, method 700 may be fused with one or more classifier cascades, and one or more beat-template matching algorithms. As an example, a classification and regression tree may be trained using the features described above, to estimate a signal quality index for a data window. Further, the estimated signal quality index based on one or more feature sets may be used to provide feedback for conditioning the pulse waveform signal. Signal conditioning (e.g., motion filtering) may be applied in order to estimate and subsequently remove components of the pulse waveform signal attributable motion and/or noise. A signal quality index may then be derived for the conditioned signal, and the conditioning algorithms adapted or adjusted based on the feedback.

In some embodiments, the methods and processes described herein may be tied to a computing system of one or more computing devices. In particular, such methods and processes may be implemented as a computer-application program or service, an application-programming interface (API), a library, and/or other computer-program product. FIG. 1 shows one, non-limiting example of a sensor-and-logic system to enact the methods and processes described herein. However, these methods and process may also be enacted on sensor-and-logic systems of other configurations and form factors, as shown schematically in FIG. 9.

Figure 9:
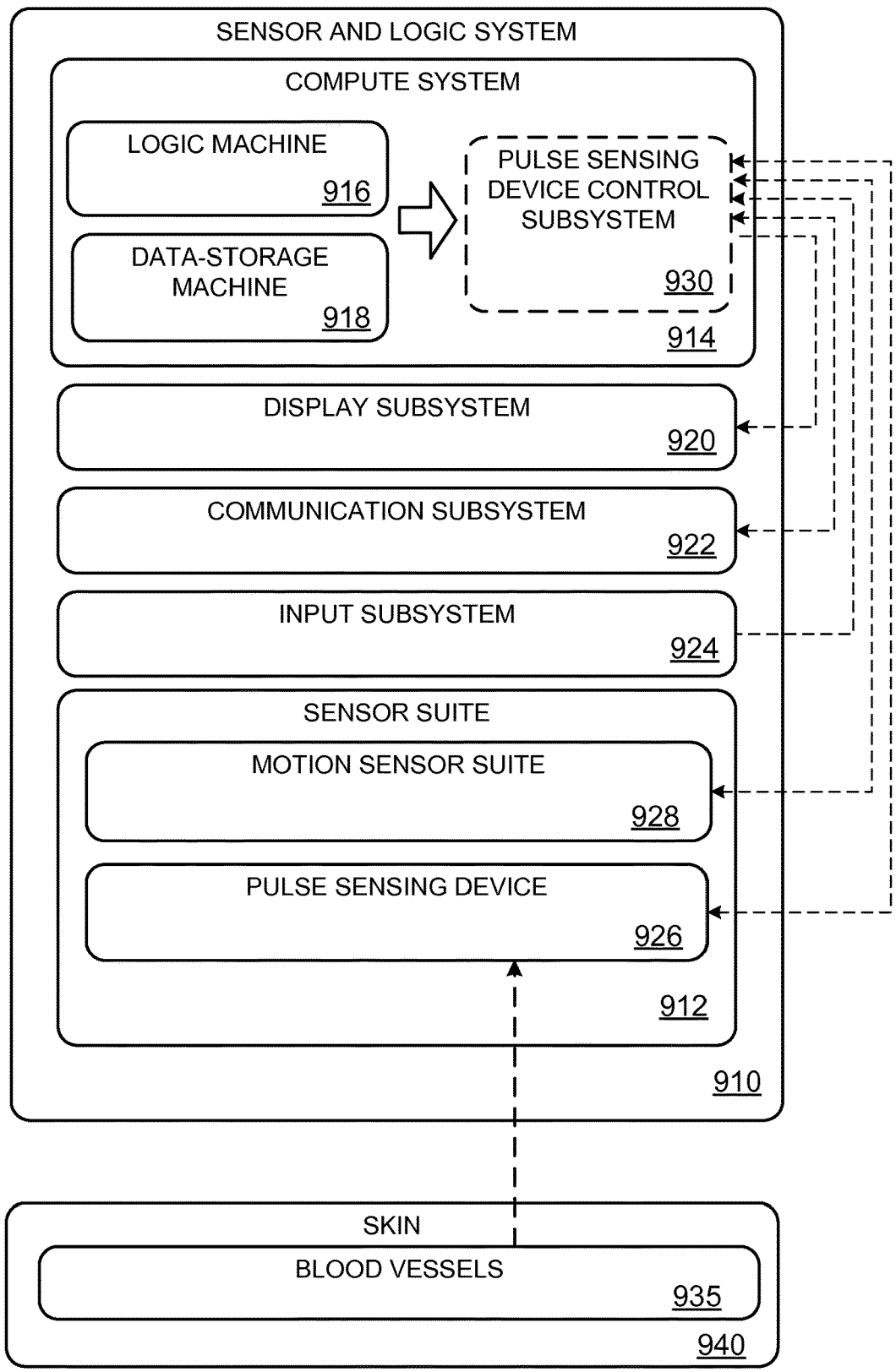
FIG. 9 schematically shows a sensor-and-logic system usable to estimate a signal quality of a transduced pressure wave received from a non-invasive pulse sensing device.

FIG. 9 schematically shows a form-agnostic sensor-and-logic system 910 that includes a sensor suite 912 operatively coupled to a compute system 914. The compute system includes a logic machine 916 and a data-storage machine 918. The compute system is operatively coupled to a display subsystem 920, a communication subsystem 922, an input subsystem 924, and/or other components not shown in FIG. 9.

Logic machine 916 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 916 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 918 includes one or more physical devices configured to hold instructions executable by logic machine 916 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

Data-storage machine 918 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 916 and data-storage machine 918 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 920 may be used to present a visual representation of data held by data-storage machine 918. This visual representation may take the form of a graphical user interface (GUI). As the herein described methods and processes change the data held by the storage machine, and thus transform the state of the storage machine, the state of display subsystem 920 may likewise be transformed to visually represent changes in the underlying data. Display subsystem 920 may include one or more display subsystem devices utilizing virtually any type of technology. Such display subsystem devices may be combined with logic machine 916 and/or data-storage machine 918 in a shared enclosure, or such display subsystem devices may be peripheral display subsystem devices. Display 34 of FIG. 1 is an example of display subsystem 920.

Communication subsystem 922 may be configured to communicatively couple compute system 914 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 36 of FIG. 1 is an example of communication subsystem 922.

Input subsystem 924 may comprise or interface with one or more user-input devices such as a keyboard, touch screen, button, dial, joystick, or switch. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition. Push button 48 of FIG. 1 is an example of input subsystem 924.

Sensor suite 912 may include one or more different sensors—e.g., pulse sensing device 926, a touch-screen sensor, push-button sensor, microphone, visible-light sensor, ultraviolet sensor, ambient-temperature sensor, contact sensors, and/or GPS receiver—as described above with reference to FIG. 1. Sensor suite 912 may include motion sensor suite 928. Motion sensor suite 928 may include one or more of an accelerometer, gyroscope, magnetometer, or other suitable motion detectors.

As described herein, pulse sensing device 926 may include one or more arterial tonometers and/or one or more optical pulse sensing devices. Compute system 914 may include pulse sensing device control subsystem 930, which may be communicatively coupled to logic machine 916 and data-storage machine 918. When pulse sensing device 926 includes an arterial tonometer, the tonometer may include one or more pressure transducers comprising one or more piezo-resistive sensors configured to provide absolute pressure signals to compute system 914 via an analog-to-digital converter. When included, the pressure transducer may be configured to transduce pressure waves from blood vessels 935 (e.g., a radial artery) through the skin 940 of the user.

In some examples, when pulse sensing device 926 includes an optical pulse sensing device, the optical pulse sensing device may include one or more optical sources comprising one or more LED emitters, and one or more optical sensors comprising one or more photodiodes matched to detect light at frequencies that are based on the frequencies of light output by the optical source. When included, the optical source(s) may be configured to illuminate one or more blood vessels 935 through the skin 940 of the user, and the optical sensor(s) may be configured to measure illumination reflected from or transmitted through blood vessels 935.

Pulse sensing device control subsystem 930 may further process the raw signals to determine pulse waveform signal quality, heart rate, blood pressure, caloric expenditures, etc. Processed signals may be stored and output via compute system 914, for example via display subsystem 920 and/or communication subsystem 922. Control signals sent to pulse sensing device 926 may be based on signals derived from sensor suite 912, information stored in data-storage machine 918, input received from communication subsystem 922, input received from input subsystem 924, etc.

In an example, a method for a wearable cardiovascular monitoring device comprises: receiving a pulse waveform from a pulse sensing device; using a first classifier, computer-analyzing a first data window of the pulse waveform signal, comprising a first number of samples; responsive to computer-analysis of the first data window indicating correct pulse sensing device placement, providing user feedback, via a feedback machine, indicating an initial level of confidence that the pulse sensing device is correctly placed; using a second classifier, computer-analyzing a second data window of the pulse waveform signal, comprising a second number of samples larger than the first number of samples; and responsive to computer-analysis of the second data window indicating correct pulse sensing device placement, providing user feedback, via the feedback machine, indicating an increased level of confidence that the pulse sensing device is correctly placed. In this example or any other example, the method further comprises: using a final classifier, computer-analyzing a final data window of the pulse waveform signal, having a final number of samples larger than the second number of samples; and responsive to computer-analysis of the final data window indicating correct pulse sensing device placement, providing user feedback, via the feedback machine, indicating that the pulse sensing device is correctly placed at a target sensing location. In this example or any other example, the method further comprises: responsive to computer-analysis of the final data window indicating correct pulse sensing device placement, computer-calculating a cardiovascular parameter based on the pulse waveform signal. In this example or any other example, the samples comprised in the second data window comprise all of the samples comprised in the first data window, and the samples comprised in the final data window comprise all of the samples comprised in the second data window. In this example or any other example, the second classifier has a lower false-positive rate than the first classifier, and the final classifier has a lower false-positive rate than the second classifier. In this example or any other example, the method further comprises: responsive to computer-analysis of the first, second, or final data window not indicating correct pulse sensing device placement, providing user feedback, via the feedback machine, indicating incorrect pulse sensing device placement. In this example or any other example, the method further comprises: responsive to computer-analysis of the first, second, or final data window not indicating correct pulse sensing device placement, computer-analyzing with the first classifier a new data window of the pulse waveform signal, comprising the first number of samples. In this example or any other example, the method further comprises: computer-determining whether the pulse waveform signal comprises an initial signal characteristic; responsive to the pulse waveform signal comprising the initial signal characteristic, providing a new data window to the first classifier comprising the first number of samples of the pulse waveform signal; and responsive to the pulse waveform signal not comprising the initial signal characteristic, providing user feedback, via the feedback machine, indicating that the pulse sensing device needs to be relocated towards a target sensing location.

In an example, a method for a wearable cardiovascular device comprises: receiving a pulse waveform signal from a pulse sensing device; computer-processing a window of the pulse waveform signal including n samples; computer-quantizing each of the n samples into an integer ranging from 1 to r; establishing a transition matrix for the window, the transition matrix including r rows and r columns, wherein each cell of the transition matrix indicates a frequency within the window that a sample m, having a quantized row value of r, is followed by a sample m+1 having a quantized column value of r; and computer-determining a signal quality index of the window based on the transition matrix. In this example or any other example, the n samples are downsampled from a raw pulse waveform signal. In this example or any other example, the raw pulse waveform signal is bandpass filtered, but not motion filtered prior to downsampling. In this example or any other example, the raw pulse waveform signal is output by an optical pulse sensing device. In this example or any other example, the raw pulse waveform signal is output by an arterial tonometer. In this example or any other example, the n samples are locally normalized prior to being quantized. In this example or any other example, the window is excluded from downstream cardiovascular parameter calculations requiring a signal quality index greater than the computer-determined signal quality index for the window. In this example or any other example, the window is included in downstream cardiovascular parameter calculations requiring a signal quality index lower than the computer-determined signal quality index for the window.

In an example, a wearable cardiovascular monitoring device comprises: a pulse sensing device; a feedback machine; and a pulse sensing device control subsystem, configured to: receive a pulse waveform signal from the pulse sensing device; using a first classifier, computer-analyze a first data window of the pulse waveform signal, the first data window comprising a first number of samples; responsive to computer-analysis of the first data window indicating correct pulse sensing device placement, provide user feedback, via the feedback machine, indicating an initial level of confidence that the pulse sensing device is correctly placed; using a second classifier having a lower false-positive rate than the first classifier, computer-analyze a second data window of the pulse waveform signal, the second data window comprising a second number of samples, larger than the first number of samples; and responsive to computer-analysis of the second data window indicating correct pulse sensing device placement, provide user feedback, via the feedback machine, indicating an increased level of confidence that the pulse sensing device is correctly placed. In this example or any other example, the pulse sensing device control subsystem is further configured to: using a final classifier having a lower false-positive rate than the second classifier, computer-analyze a final data window of the pulse waveform signal, having a final number of samples larger than the second number of samples; responsive to computer-analysis of the final data window indicating correct pulse sensing device placement, provide user feedback, via the feedback machine, indicating that the pulse sensing device is correctly placed; and responsive to computer-analysis of the final data window indicating correct pulse sensing device placement, computer-calculate a cardiovascular parameter based on the pulse waveform signal. In this example or any other example, the samples comprised in the second data window comprise all of the samples in the first data window, and the samples comprised in the final data window include all of the samples comprised in the second data window. In this example or any other example, the pulse sensing device control subsystem is further configured to: responsive to computer-analysis of the first, second, or final data window not indicating correct pulse sensing device placement, provide user feedback, via the feedback machine, indicating incorrect pulse sensing device placement; and responsive to computer-analysis of the first, second, or final data window indicating incorrect pulse sensing device placement, computer-analyze with the first classifier a new data window of the pulse waveform signal, the new data window comprising the first number of samples.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method for a wearable cardiovascular monitoring device, comprising:
   operating a pulse sensing device adjacent to an artery of a user wearing the wearable cardiovascular monitoring device;
   receiving a pulse waveform signal from the pulse sensing device;
   using a first classifier, computer-analyzing a first data window of the pulse waveform signal, comprising a first number of samples;
   responsive to computer-analysis of the first data window indicating correct pulse sensing device placement, providing user feedback, via a feedback machine, indicating an initial level of confidence that the pulse sensing device is correctly placed;
   using a second classifier, computer-analyzing a second data window of the pulse waveform signal, comprising a second number of samples larger than the first number of samples; and
   responsive to computer-analysis of the second data window indicating correct pulse sensing device placement, providing user feedback, via the feedback machine, indicating an increased level of confidence that the pulse sensing device is correctly placed.

2. The method of claim 1, further comprising:

using a final classifier, computer-analyzing a final data window of the pulse waveform signal, having a final number of samples larger than the second number of samples; and responsive to computer-analysis of the final data window indicating correct pulse sensing device placement, providing user feedback, via the feedback machine, indicating that the pulse sensing device is correctly placed at a target sensing location.

3. The method of claim 2, further comprising:

responsive to computer-analysis of the final data window indicating correct pulse sensing device placement, computer-calculating a cardiovascular parameter based on the pulse waveform signal.

4. The method of claim 2, wherein the samples comprised in the second data window comprise all of the samples comprised in the first data window, and wherein the samples comprised in the final data window comprise all of the samples comprised in the second data window.

5. The method of claim 2, wherein the second classifier has a lower false-positive rate than the first classifier, and wherein the final classifier has a lower false-positive rate than the second classifier.

6. The method of claim 1, further comprising:

responsive to computer-analysis of the first, second, or final data window not indicating correct pulse sensing device placement, providing user feedback, via the feedback machine, indicating incorrect pulse sensing device placement.

7. The method of claim 6, further comprising:

responsive to computer-analysis of the first, second, or final data window not indicating correct pulse sensing device placement, computer-analyzing with the first classifier a new data window of the pulse waveform signal, comprising the first number of samples.

8. The method of claim 1, further comprising:

computer-determining whether the pulse waveform signal comprises an initial signal characteristic;

responsive to the pulse waveform signal comprising the initial signal characteristic, providing a new data window to the first classifier comprising the first number of samples of the pulse waveform signal; and responsive to the pulse waveform signal not comprising the initial signal characteristic, providing user feedback, via the feedback machine, indicating that the pulse sensing device needs to be relocated towards a target sensing location.

9. A method for a wearable cardiovascular monitoring device, comprising:

operating a pulse sensing device adjacent to an artery of a user wearing the wearable cardiovascular monitoring device;

receiving a pulse waveform signal from the pulse sensing device;

computer-processing a window of the pulse waveform signal including n samples;

computer-quantizing each of the n samples into an integer ranging from 1 to r;

establishing a transition matrix for the window, the transition matrix including r rows and r columns, wherein each cell of the transition matrix indicates a frequency within the window that a sample m, having a quantized row value of r, is followed by a sample m+1 having a quantized column value of r; and computer-determining a signal quality index of the window based on the transition matrix.

10. The method of claim 9, wherein the n samples are downsampled from a raw pulse waveform signal.

11. The method of claim 10, wherein the raw pulse waveform signal is bandpass filtered, but not motion filtered prior to downsampling.

12. The method of claim 10, wherein the raw pulse waveform signal is output by an optical pulse sensing device.

13. The method of claim 10, wherein the raw pulse waveform signal is output by an arterial tonometer.

14. The method of claim 9, wherein the n samples are locally normalized prior to being quantized.

15. The method of claim 9, wherein the window is excluded from downstream cardiovascular parameter calculations requiring a signal quality index greater than the computer-determined signal quality index for the window.

16. The method of claim 9, wherein the window is included in downstream cardiovascular parameter calculations requiring a signal quality index lower than the computer-determined signal quality index for the window.

17. A wearable cardiovascular monitoring device, comprising:

a pulse sensing device;

a feedback machine; and a pulse sensing device control subsystem, configured to:
receive a pulse waveform signal from the pulse sensing device;

using a first classifier, computer-analyze a first data window of the pulse waveform signal, the first data window comprising a first number of samples;

responsive to computer-analysis of the first data window indicating correct pulse sensing device placement, provide user feedback, via the feedback machine, indicating an initial level of confidence that the pulse sensing device is correctly placed;

using a second classifier having a lower false-positive rate than the first classifier, computer-analyze a second data window of the pulse waveform signal, the second data window comprising a second number of samples, larger than the first number of samples; and responsive to computer-analysis of the second data window indicating correct pulse sensing device placement, provide user feedback, via the feedback machine, indicating an increased level of confidence that the pulse sensing device is correctly placed.

18. The wearable cardiovascular monitoring device of claim 17, wherein the pulse sensing device control subsystem is further configured to:

using a final classifier having a lower false-positive rate than the second classifier, computer-analyze a final data window of the pulse waveform signal, having a final number of samples larger than the second number of samples;

responsive to computer-analysis of the final data window indicating correct pulse sensing device placement, provide user feedback, via the feedback machine, indicating that the pulse sensing device is correctly placed; and responsive to computer-analysis of the final data window indicating correct pulse sensing device placement, computer-calculate a cardiovascular parameter based on the pulse waveform signal.

19. The wearable cardiovascular monitoring device of claim 18, wherein the samples comprised in the second data window comprise all of the samples in the first data window, and wherein the samples comprised in the final data window include all of the samples comprised in the second data window.

20. The wearable cardiovascular monitoring device of claim 18, wherein the pulse sensing device control subsystem is further configured to:
  responsive to computer-analysis of the first, second, or final data window not indicating correct pulse sensing device placement, provide user feedback, via the feedback machine, indicating incorrect pulse sensing device placement; and
  responsive to computer-analysis of the first, second, or final data window indicating incorrect pulse sensing device placement, computer-analyze with the first classifier a new data window of the pulse waveform signal, the new data window comprising the first number of samples.

* * * * *